US011338084B2

(12) United States Patent
Meyer et al.

(10) Patent No.: US 11,338,084 B2
(45) Date of Patent: May 24, 2022

(54) APPARATUS FOR SUBRETINAL ADMINISTRATION OF THERAPEUTIC AGENT VIA A CURVED NEEDLE

(71) Applicant: Gyroscope Therapeutics Limited, London (GB)

(72) Inventors: Thomas E. Meyer, Philadelphia, PA (US); Benjamin L. Ko, Cincinnati, OH (US); Isaac J. Khan, Bridgewater, NJ (US); Daniel W. Price, Loveland, OH (US); Brendan J. Oberkircher, Cincinnati, OH (US); Michael F. Keane, Downingtown, PA (US)

(73) Assignee: Gyroscope Therapeutics Limited, London (GB)

( * ) Notice: Subject to any disclaimer, the term of this patent is extended or adjusted under 35 U.S.C. 154(b) by 353 days.

(21) Appl. No.: 16/599,206

(22) Filed: Oct. 11, 2019

(65) Prior Publication Data

US 2020/0078514 A1 Mar. 12, 2020

Related U.S. Application Data

(62) Division of application No. 15/438,918, filed on Feb. 22, 2017, now Pat. No. 10,478,553.
(Continued)

(51) Int. Cl.
*A61M 5/158* (2006.01)
*A61F 9/00* (2006.01)
(Continued)

(52) U.S. Cl.
CPC .......... *A61M 5/158* (2013.01); *A61F 9/0008* (2013.01); *A61F 9/0026* (2013.01); *A61M 5/168* (2013.01);
(Continued)

(58) Field of Classification Search
CPC ........ A61F 9/00; A61F 9/0008; A61F 9/0017; A61F 9/0026; A61F 9/00736;
(Continued)

(56) References Cited

U.S. PATENT DOCUMENTS 5,354,279 A 10/1994 Hofling
5,409,457 A 4/1995 del Cerro et al.
(Continued)

FOREIGN PATENT DOCUMENTS

CN 1204242 A 1/1999
CN 101052434 A 10/2007
(Continued)

OTHER PUBLICATIONS

Chinese Office Action and Search Report dated Apr. 21, 2020 for Application No. 201780016408.X, 14 pages.
(Continued)

*Primary Examiner* — Kami A Bosworth
(74) *Attorney, Agent, or Firm* — Frost Brown Todd LLC

(57) ABSTRACT

An apparatus includes a body, a cannula, and a needle. The cannula is flexible and extends distally from the body. The needle is slidably disposed in the cannula. The needle includes a sharp distal tip and a curved portion. The needle is configured to translate relative to the cannula between a proximal position and a distal position. The distal tip is configured to be positioned inside the cannula when the needle is in the proximal position. The distal tip is configured to be positioned outside the cannula when the needle is in the distal position. The needle is resiliently biased to extend along a curve through the curved portion.

20 Claims, 22 Drawing Sheets

Related U.S. Application Data

(60) Provisional application No. 62/305,767, filed on Mar. 9, 2016.

(51) Int. Cl.
*A61M 5/168* (2006.01)
*A61M 5/32* (2006.01)

(52) U.S. Cl.
CPC ............ *A61F 9/0017* (2013.01); *A61M 5/329* (2013.01); *A61M 2005/1585* (2013.01); *A61M 2205/582* (2013.01); *A61M 2210/0612* (2013.01)

(58) Field of Classification Search
CPC .... A61M 5/158; A61M 5/3287; A61M 5/329; A61M 2025/0087; A61M 2025/0092; A61M 2025/0096; A61M 2210/0612
See application file for complete search history.

(56) References Cited

U.S. PATENT DOCUMENTS

| | | | |
|---|---|---|---|
| 5,964,740 | A | 10/1999 | Ouchi |
| 6,190,353 | B1 | 2/2001 | Makower et al. |
| 6,217,554 | B1 | 4/2001 | Green |
| 6,231,546 | B1 | 5/2001 | Milo et al. |
| 6,368,315 | B1 | 4/2002 | Gillis et al. |
| 6,413,245 | B1 | 7/2002 | Yaacobi et al. |
| 6,761,724 | B1 | 7/2004 | Zrenner et al. |
| 6,824,532 | B2 | 11/2004 | Gillis et al. |
| 7,189,245 | B2 | 3/2007 | Kaplan |
| 7,207,980 | B2 | 4/2007 | Christian et al. |
| 7,413,734 | B2 | 8/2008 | Mistry et al. |
| 8,197,435 | B2 | 6/2012 | Prausnitz et al. |
| 8,226,619 | B2 | 7/2012 | Cupertino |
| 8,425,473 | B2 | 4/2013 | Ho et al. |
| 10,478,553 | B2 | 11/2019 | Meyer et al. |
| 2002/0143302 | A1 | 10/2002 | Hinchliffe et al. |
| 2004/0039253 | A1* | 2/2004 | Peyman .............. A61F 9/00727 600/201 |
| 2004/0138562 | A1 | 7/2004 | Makower et al. |
| 2004/0199130 | A1 | 10/2004 | Chornenky et al. |
| 2005/0143363 | A1 | 6/2005 | de Juan et al. |
| 2006/0025720 | A1 | 2/2006 | Sawa et al. |
| 2006/0293647 | A1 | 12/2006 | McRae et al. |
| 2008/0004596 | A1 | 1/2008 | Yun et al. |
| 2008/0058704 | A1 | 3/2008 | Hee et al. |
| 2008/0281292 | A1 | 11/2008 | Hickingbotham et al. |
| 2010/0004499 | A1 | 1/2010 | Brigatti et al. |
| 2010/0145278 | A1 | 6/2010 | Magana |
| 2010/0305514 | A1 | 12/2010 | Valenti et al. |
| 2012/0071832 | A1 | 3/2012 | Bunch |
| 2012/0191064 | A1 | 7/2012 | Conston et al. |
| 2012/0271272 | A1 | 10/2012 | Hammack et al. |
| 2012/0323220 | A1 | 12/2012 | Mackay, II et al. |
| 2013/0103026 | A1 | 4/2013 | Kleshinski et al. |
| 2013/0211379 | A1 | 8/2013 | Clair et al. |
| 2013/0216623 | A1 | 8/2013 | Yamamoto et al. |
| 2013/0245600 | A1 | 9/2013 | Yamamoto et al. |
| 2014/0121641 | A1 | 5/2014 | Fischell et al. |
| 2015/0164687 | A1* | 6/2015 | Kashani ............... A61F 9/0008 604/506 |
| 2015/0209180 | A1 | 7/2015 | Prausnitz et al. |
| 2015/0223977 | A1 | 8/2015 | Oberkircher et al. |
| 2015/0258120 | A1 | 9/2015 | Zarnitsyn et al. |
| 2015/0351958 | A1 | 12/2015 | Contiliano et al. |
| 2015/0351959 | A1 | 12/2015 | Clem et al. |
| 2016/0074211 | A1 | 3/2016 | Ko et al. |
| 2016/0074212 | A1 | 3/2016 | Price et al. |
| 2016/0074217 | A1 | 3/2016 | Price et al. |
| 2016/0081849 | A1 | 3/2016 | Tsai et al. |
| 2017/0095369 | A1 | 4/2017 | Andino et al. |
| 2017/0333416 | A1 | 11/2017 | Zarnitsyn et al. |
| 2018/0042765 | A1 | 2/2018 | Noronha et al. |

FOREIGN PATENT DOCUMENTS

| | | |
|---|---|---|
| EP | 3088027 A1 | 11/2016 |
| RU | 2014131467 A | 2/2016 |
| WO | WO 2012/177398 A2 | 12/2012 |
| WO | WO 2013/022614 A2 | 2/2013 |
| WO | WO 2015/126694 A1 | 8/2015 |
| WO | WO 2015/187629 A1 | 12/2015 |
| WO | WO 2017/042584 A1 | 3/2017 |

OTHER PUBLICATIONS

European Communication dated Feb. 11, 2020 for Application No. 17712635.6, 4 pages.
International Search Report and Written Opinion dated Jun. 7, 2017 for International Application No. PCT/US2017/021508, 12 pages.
International Preliminary Report on Patentability dated Sep. 11, 2018 for International Application No. PCT/US2017/021508, 8 pages.
U.S. Appl. No. 62/305,767, filed Mar. 9, 2016.
Kang, Se Woong, et al. "A new instrument for drainage or injection of fluid within subretinal space."*Retina* 23.5 (2003): 661-666.
Komáromy, András M., et al. "Application of a new subretinal injection device in the dog." *Cell transplantation* 15.6 (2006): 511-519.
Olsen, Timothy W., et al. "Cannulation of the suprachoroidal space: a novel drug delivery methodology to the posterior segment." *American journal of ophthalmology* 142.5 (2006): 777-787.
Patel, Samirkumar R., et al. "Suprachoroidal drug delivery to the back of the eye using hollow microneedles." *Pharmaceutical research* 28.1 (2011): 166-176.
Schanze, Thomas, et al. "Implantation and testing of subretinal film electrodes in domestic pigs." *Experimental eye research* 82.2 (2006): 332-340.
Japanese Notification of Reasons for Refusal dated Mar. 6, 2020 for Application No. 2018-567011, 6 pages.
Japanese Decision of Refusal dated Sep. 2, 2020 for Application No. 2018-567011, 4 pages.
Korean Office Action dated Jul. 7, 2020 for Application No. 10-2018-7028153, 4 pages.
Russian Office Action dated Jun. 11, 2020 for Application No. 2018135286, 7 pages.
Patel, S. R., et al. "Intraocular Pharmacokinetics of Suprachoroidal Drug Delivery Administered Using Hollow Microneedles." *Investigative Ophthalmology & Visual Science* 51.13 (2010): Abstract only.
Patel, S. R., et al. "Suprachoroidal drug delivery to the back of the eye using hollow microneedles." *Pharmaceutical research* 28.1 (2011): 166-176.
Patel, S., et al. "Suprachoroidal Drug Delivery Using Microneedles." *Investigative Ophthalmology & Visual Science* 49.13 (2008): Abstract Only.
Peden, Marc C., et al. "Ab-externo AAV-mediated gene delivery to the suprachoroidal space using a 250-micron flexible microcatheter." *PLoS One* 6.2 (2011): e17140.
Peden, M. C., et al. "Safety Study of Ab-Externo AAV Gene Therapy Delivery to the Subretinal and Suprachoroidal Space Using a 250 Micron Flexible Microcatheter." *Investigative Ophthalmology & Visual Science* 50.13 (2009):Abstract only.
Soni, M. H., and A. K. Tyagi. "Induction of Choroidal Detachment: A New Surgical Technique for Choroidal Biopsy." *Investigative Ophthalmology & Visual Science* 46.13 (2005): Abstract only.
Tetz, Manfred, Stanislao Rizzo, and Albert J. Augustin. "Safety of submacular suprachoroidal drug administration via a microcatheter: retrospective analysis of European treatment results." *Ophthalmologica* 227.4 (2012): 183-189.

\* cited by examiner

APPARATUS FOR SUBRETINAL ADMINISTRATION OF THERAPEUTIC AGENT VIA A CURVED NEEDLE

PRIORITY

This application is a divisional of U.S. Non-Provisional patent application Ser. No. 15/438,918, entitled "Apparatus for Subretinal Administration of Therapeutic Agent via a Curved Needle," filed Feb. 22, 2017, issued as U.S. Pat. No. 10,478,553 on Nov. 19, 2019; which claims priority to U.S. Provisional Patent Application No. 62/305,767, entitled "Curved Needle Choroidal Penetration," filed Mar. 9, 2016, the disclosure of which is incorporated by reference herein.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and in some cases may disappear as well. It may therefore be desirable to provide treatment for macular degeneration in order to prevent or reverse the loss of vision caused by macular degeneration. In some cases it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
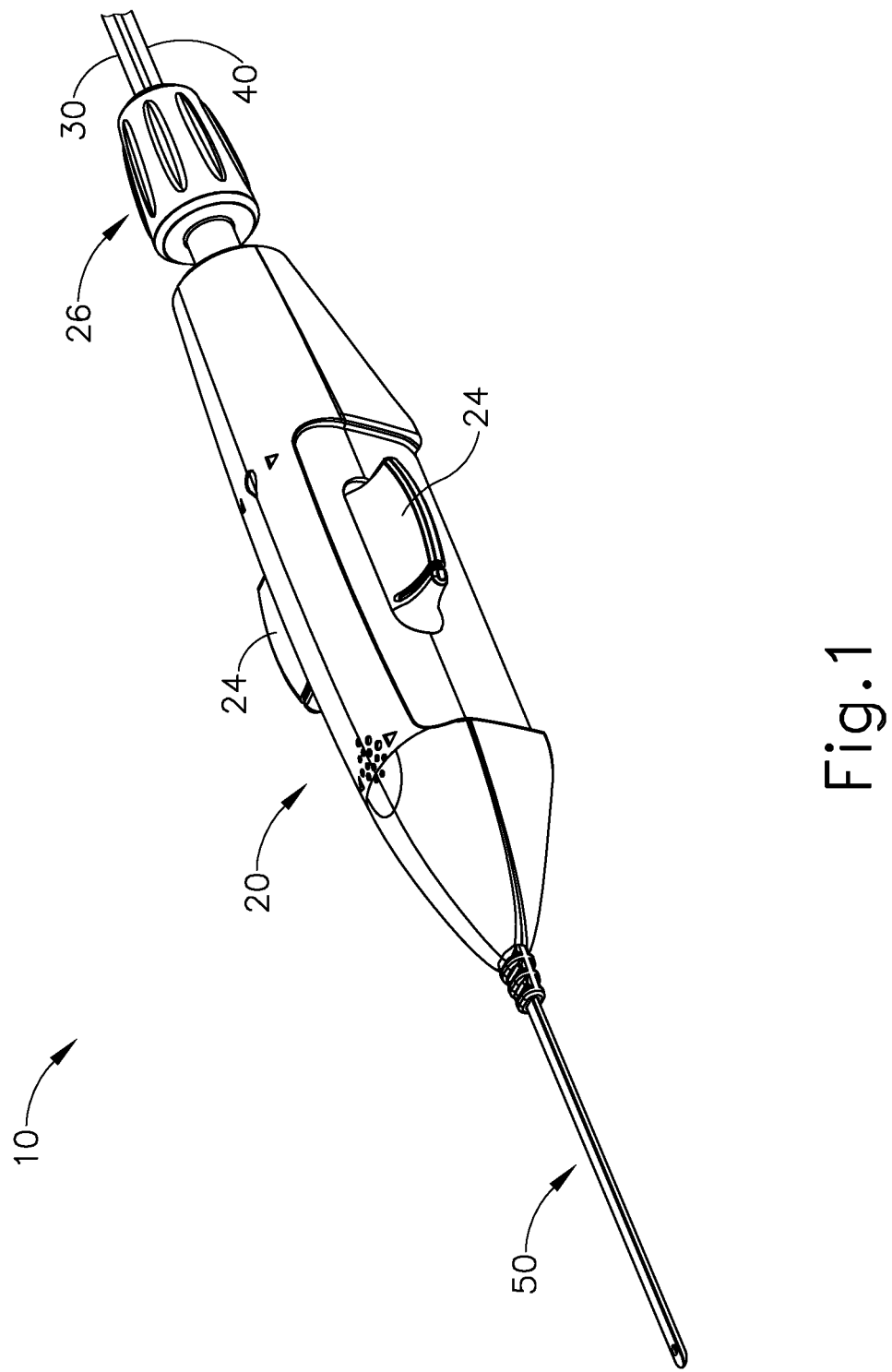
FIG. 1 depicts a perspective view of an exemplary instrument for subretinal administration of a therapeutic agent from a suprachoroidal approach.
Figure 2:
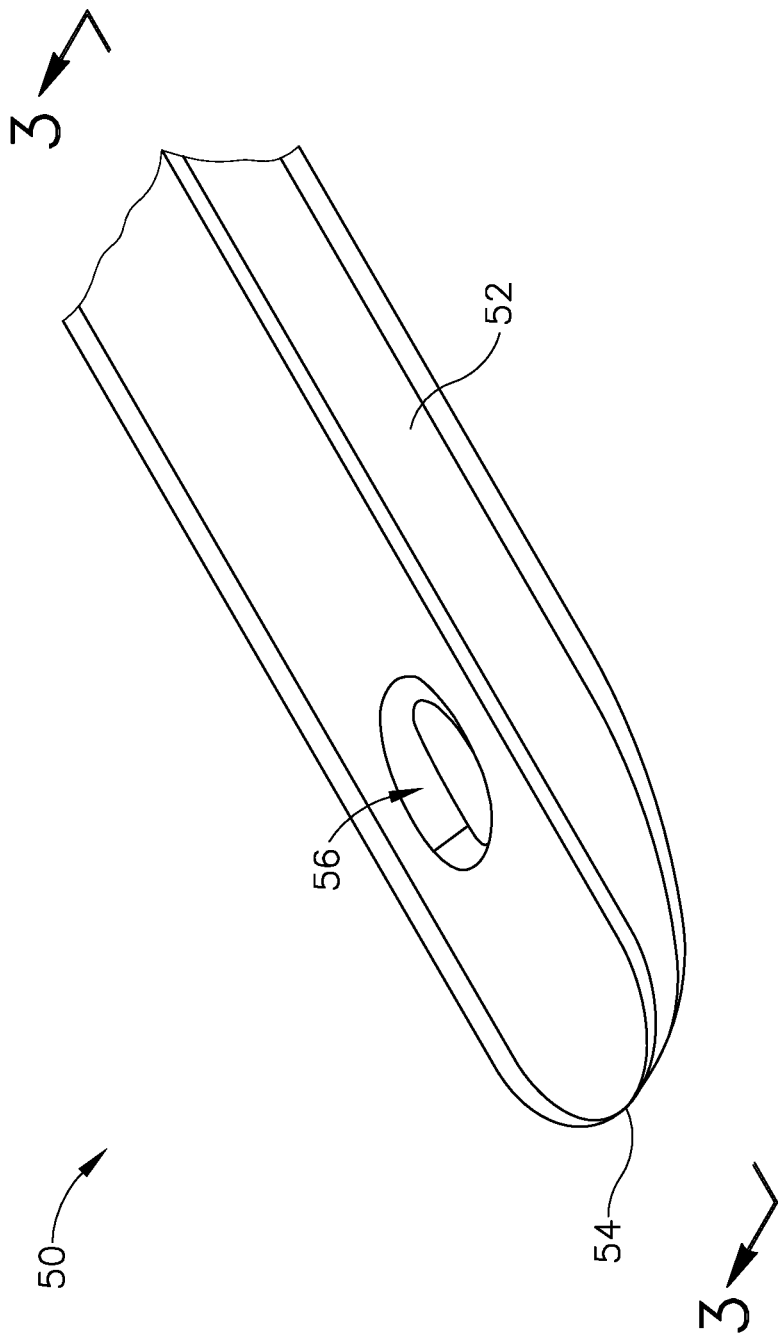
FIG. 2 depicts a perspective view of the distal end of an exemplary cannula that may be incorporated into the instrument of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. EXEMPLARY INSTRUMENT FOR SUBRETINAL ADMINISTRATION OF THERAPEUTIC AGENT

FIG. 1 shows an exemplary instrument (10) that is configured for use in a procedure for the subretinal administration of a therapeutic agent to an eye of a patient from a suprachoroidal approach. Instrument (10) comprises a body (20) and a flexible cannula (50) extending distally from body (20). Cannula (50) of the present example has a generally rectangular cross section, though any other suitable cross-sectional profile (e.g., elliptical, etc.) may be used. Cannula (50) is generally configured to support a needle (100) that is slidable within cannula (50), as will be described in greater detail below. In some examples, such a rectangular shape may prevent cannula (50) from rotating as it is inserted into a patient's eye. As will be understood, such a feature may be desirable such that a needle (100) may exit from cannula (50) in a predictable direction.

In the present example, cannula (50) comprises a flexible material such as Polyether block amide (PEBA), which may be manufactured under the trade name PEBAX. Of course, any other suitable material or combination of materials may be used. Also in the present example, cannula (50) has a cross-sectional profile dimension of approximately 2.0 mm by 0.8 mm, with a length of approximately 80 mm. Alternatively, any other suitable dimensions may be used. As will be described in greater detail below, cannula (50) is flexible enough to conform to specific structures and contours of the patient's eye, yet cannula (50) has sufficient column strength to permit advancement of cannula (50) between the sclera and choroid of patient's eye without buckling. By way of example only, cannula (50) may be configured and operable in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein.

Figure 3A:
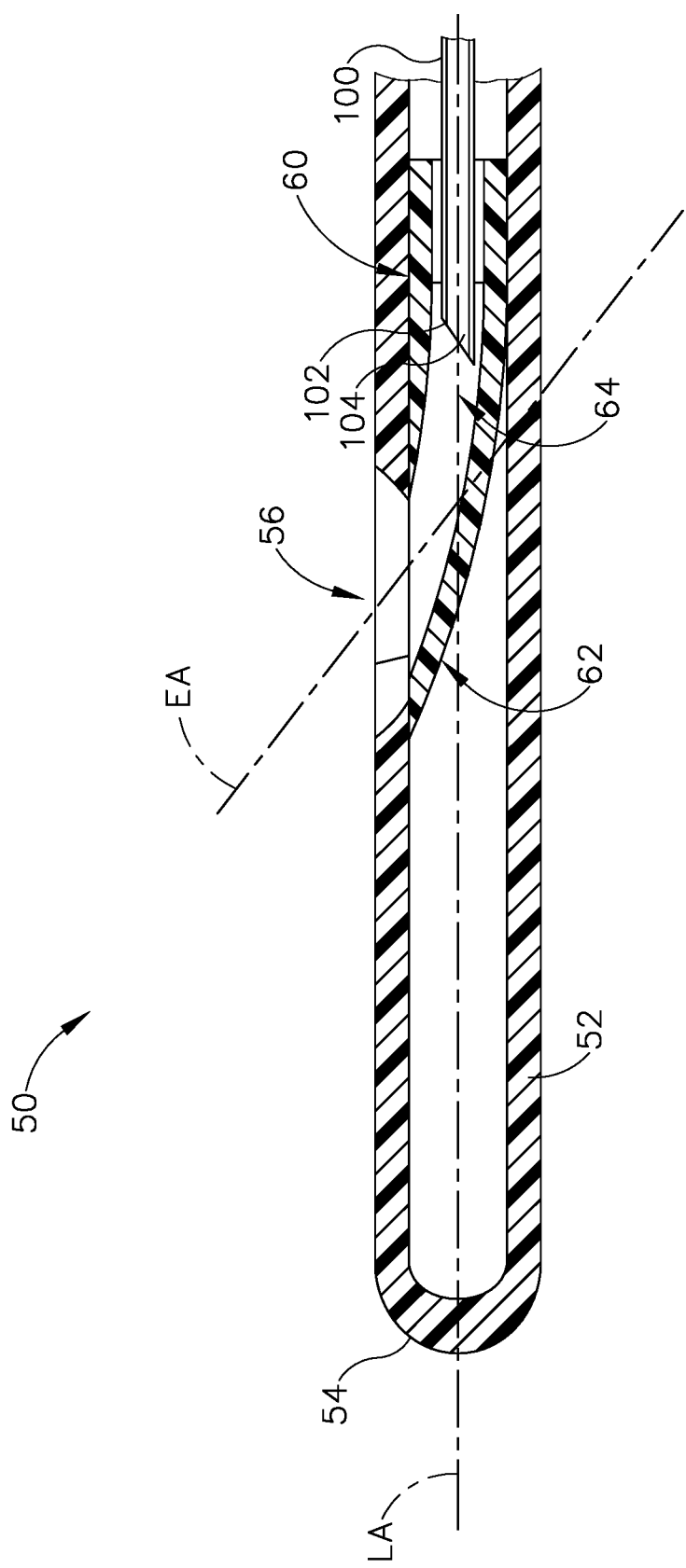
FIG. 3A depicts a cross-sectional side view of the cannula of FIG. 2, with the cross-section taken along line 3-3 of FIG. 2, with a needle in a first longitudinal position.
Figure 3B:
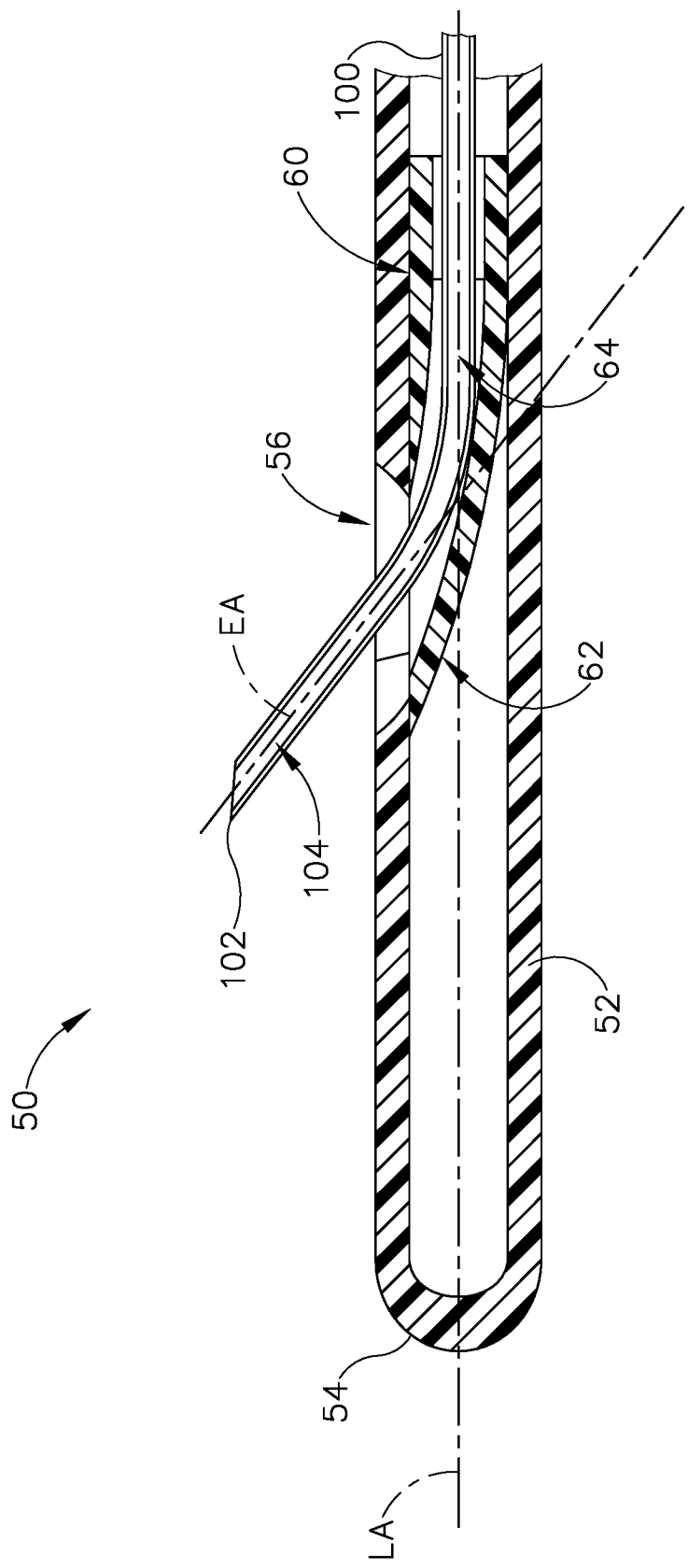
FIG. 3B depicts a cross-sectional side view of the cannula of FIG. 2, with the cross-section taken along line 3-3 of FIG. 2, with the needle in a second longitudinal position.

As can be seen in FIGS. 2-3B and 6, cannula (50) comprises a body (52), a closed distal end (54), and a lateral opening (56) that is located proximal to distal end (54). In the present example, distal end (54) has a rounded configuration. It should be understood that distal end (54) may have any suitable kind of curvature. It should also be understood that distal end (54) may have any other suitable kind of configuration (e.g., beveled, etc.). In the present example, distal end (54) is configured to provide separation between the sclera and choroid layers to enable cannula (50) to be advanced between such layers while not inflicting trauma to the sclera or choroid layers. Also in the present example, the region of body (52) that defines lateral opening (56) is beveled, as best seen in FIGS. 3A-3B. Alternatively, the edge of lateral opening (56) may have any other suitable configuration.

As best seen in FIGS. 3A-3B, a needle guide (60) is disposed within the hollow interior of cannula (50). By way of example only, needle guide (60) may be secured within cannula (50) by a press or interference fit, by adhesives, by mechanical locking mechanisms, and/or in any other suitable fashion. Needle guide (60) includes a curved distal end (62) that leads to lateral opening (56) of cannula (50), such that a lumen (64) of needle guide (60) distally terminates at lateral opening (56). The portion of needle guide (60) that is proximal to distal end (62) is substantially straight. Needle guide (60) may be formed of plastic, stainless steel, and/or any other suitable biocompatible material(s).

Needle (100) of the present example has a sharp distal tip (102) and defines a lumen (104). Distal tip (102) of the present example has a lancet configuration. In some other versions, distal tip (102) has a tri-bevel configuration or any other configuration as described in U.S. Pub. No. 2015/0223977, entitled "Method and Apparatus for Subretinal Administration of Therapeutic Agent," published Aug. 13, 2015, the disclosure of which is incorporated by reference herein. Still other suitable forms that distal tip (102) may take will be apparent to those of ordinary skill in the art in view of the teachings herein. Needle (100) of the present example comprises a stainless steel hypodermic needle that is sized to deliver the therapeutic agent while being small enough to minimize incidental trauma as needle (100) penetrates tissue structures of the patient's eye, as will be described in greater detail below. While stainless steel is used in the present example, it should be understood that any other suitable material(s) may be used, including but not limited to nitinol, etc.

By way of example only, needle (100) may be 35 gauge with a 100 μm inner diameter, although other suitable sizes may be used. For instance, the outer diameter of needle (100) may fall within the range of 27 gauge to 45 gauge; or more particularly within the range of 30 gauge to 42 gauge; or more particularly within the range of 32 gauge to 39 gauge. As another merely illustrative example, the inner diameter of needle (100) may fall within the range of approximately 50 μm to approximately 200 μm; or more particularly within the range of approximately 50 μm to approximately 150 μm; or more particularly within the range of approximately 75 μm to approximately 125 μm.

Needle (100) is slidably disposed within lumen (64) of needle guide (60). Needle guide (60) is generally configured to direct needle (100) upwardly along an exit axis (EA) that is obliquely oriented relative to the longitudinal axis (LA) of cannula (50) through lateral opening (56) of cannula (50). This is shown in the sequence depicted in FIGS. 3A-3B, in which FIG. 3A shows needle (100) in a proximal position (where distal tip (102) of needle (100) is fully contained in lumen (64) of needle guide (60)); and FIG. 3B shows needle (100) in a distal position (where distal tip (102) of needle (100) is outside of needle guide (60)). While needle (100) is flexible, needle (100) of the present example is resiliently biased to assume a straight configuration. Thus, as shown in FIG. 3B, the portion of needle (100) that extends outside of cannula (50) and needle guide (60) is substantially straight, extending along exit axis (EA). In particular, at least a substantial length of the portion of needle (100) that extends outside of cannula (50) and needle guide (60) is coaxially aligned with exit axis (EA).

It should be understood that the depiction of exit axis (EA) in FIGS. 3A-3B may be somewhat exaggerated, for illustrative purposes only. In some versions, curved distal end (62) is configured to direct needle (100) along an exit axis (EA) that extends distally from cannula (50) at an angle of approximately 7° to approximately 9° relative to the longitudinal axis (LA) of cannula (50). It should be understood that such an angle may be desirable to deflect needle (100) in a direction to ensure penetration of needle into the choroid and to minimize the possibility of needle (100) continuing beneath the choroid through the suprachoroidal space (as opposed to penetrating through the choroid) and the possibility of retinal perforation. By way of further example only, curved distal portion (88) may urge needle (100) to exit cannula (50) along an exit axis (EA) that is oriented at an angle within the range of approximately 5° to approximately 30° relative to the longitudinal axis (LA) of cannula (50); or more particularly within the range of approximately 5° to approximately 20° relative to the longitudinal axis (LA) of cannula (50); or more particularly within the range of approximately 5° to approximately 10° relative to the longitudinal axis (LA) of cannula (50).

As shown in FIG. 1, instrument (10) of the present example further comprises an actuation knob (26) located at the proximal end of body (20). Actuation knob (26) is rotatable relative to body (20) to thereby selectively translate needle (100) longitudinally relative to cannula (50). In particular, actuation knob (26) is rotatable in a first angular direction to drive needle (100) distally relative to cannula (50); and in a second angular direction to drive needle (100) proximally relative to cannula (50). By way of example only, instrument (10) may provide such functionality through knob (26) in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein. Alternatively, any other suitable kind of actuation feature(s) may be used to drive needle (100) longitudinally relative to cannula (50).

In the present example, knob (26) is rotatable through a complete range of motion that corresponds to advancement of needle (100) to a position relative to cannula (50) to a predetermined amount of penetration within an eye of a patient. In other words, instrument (10) is configured such that an operator rotates knob (26) until knob (26) can no longer rotate, or until knob (26) begins to slip or "freewheel" in a clutch assembly, to properly position needle (100) within an eye of a patient. In some examples, the predetermined amount of advancement of needle (100) relative to cannula (50) is between approximately 0.25 mm to approximately 10 mm; or more particularly within the range of approximately 0.1 mm to approximately 10 mm; or more particularly within the range of approximately 2 mm to approximately 6 mm; or more particularly to approximately 4 mm.

In addition or in the alternative, instrument (10) may be equipped with certain tactile feedback features to indicate to an operator when needle (100) has been advanced to certain predetermined distances relative to cannula (50). Accordingly, an operator may determine the desired depth of penetration of needle (100) into a patient's eye based on direct visualization of indicia on instrument and/or based on tactile feedback from instrument (10). Of course, such tactile feedback features may be combined with the present example, as will be apparent to those of ordinary skill in the art in view of the teachings herein.

As also shown in FIG. 1, a pair of supply tubes (30, 40) extend proximally from actuator knob (26). In the present example, first supply tube (30) is configured to couple with a source of bleb fluid (340) (e.g., BSS); while second supply tube (40) is configured to couple with a source of therapeutic agent (341). It should be understood that each fluid supply tube (30, 40) may include a conventional luer feature and/or other structures permitting fluid supply tubes (30, 40) to be coupled with respective fluid sources. Fluid supply tubes (30, 40) lead to a valve assembly that includes actuation arms (24). Actuation arms (24) are pivotable to selectively change the state of the valve assembly. Based on the pivotal position of actuation arms (24), the valve assembly is operable to selectively pinch or otherwise open/close the supply of fluid from fluid supply tubes (30, 40) to lumen (104) of needle (100). Thus, actuation arms (24) are operable to selectively control the delivery of bleb fluid (340) and therapeutic agent (341) via needle (100). By way of example only, the valve assembly may be configured and operable in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein. Other suitable features and configurations that may be used to control fluid delivery via needle (100) will be apparent to those of ordinary skill in the art in view of the teachings herein.

It should be understood that the features and operability of instrument (10) may be varied in numerous ways. By way of example only, needle (100) may be replaced with needle (200) as described in greater detail below. In addition, cannula (50) may be replaced with cannula (400) as will be described in greater detail below. In addition, instrument (10) may be modified in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2015/0351958, entitled "Therapeutic Agent Delivery Device with Convergent Lumen," published Dec. 10, 2015, the disclosure of which is incorporated by reference herein; U.S. Pub. No. 2015/0351959, entitled "Sub-Retinal Tangential Needle Catheter Guide and Introducer," published Dec. 10, 2015, the disclosure of which is incorporated by reference herein; U.S. Pub. No. 2016/0074212, entitled "Method and Apparatus for Sensing Position Between Layers of an Eye," published Mar. 17, 2016, the disclosure of which is incorporated by reference herein; U.S. Pub. No. 2016/0074217, entitled "Motorized Suprachoroidal Injection of Therapeutic Agent," published Mar. 17, 2016, the disclosure of which is incorporated by reference herein; U.S. Pub. No. 2016/0074211, entitled "Therapeutic Agent Delivery Device with Advanceable Cannula and Needle," published Mar. 17, 2016, the disclosure of which is incorporated by reference herein; and/or U.S. Pub. No. 2016/0081849, entitled "Therapeutic Agent Delivery Device," published Mar. 24, 2016, the disclosure of which is incorporated by reference herein. Other suitable modifications will be apparent to those of ordinary skill in the art in view of the teachings herein.

II. EXEMPLARY PROCEDURE FOR SUBRETINAL ADMINISTRATION OF THERAPEUTIC AGENT

FIGS. 4A-5C show an exemplary procedure for subretinal delivery of therapeutic agent from a suprachoroidal approach using instrument (10) described above. By way of example only, the method described herein may be employed to treat macular degeneration and/or other ocular conditions. Although the procedure described herein is discussed in the context of the treatment of age-related macular degeneration, it should be understood that no such limitation is intended or implied. For instance, in some merely exemplary alternative procedures, the same techniques described herein may be used to treat retinitis pigmentosa, diabetic retinopathy, and/or other ocular conditions. Additionally, it should be understood that the procedure described herein may be used to treat either dry or wet age-related macular degeneration.

Figure 4A:
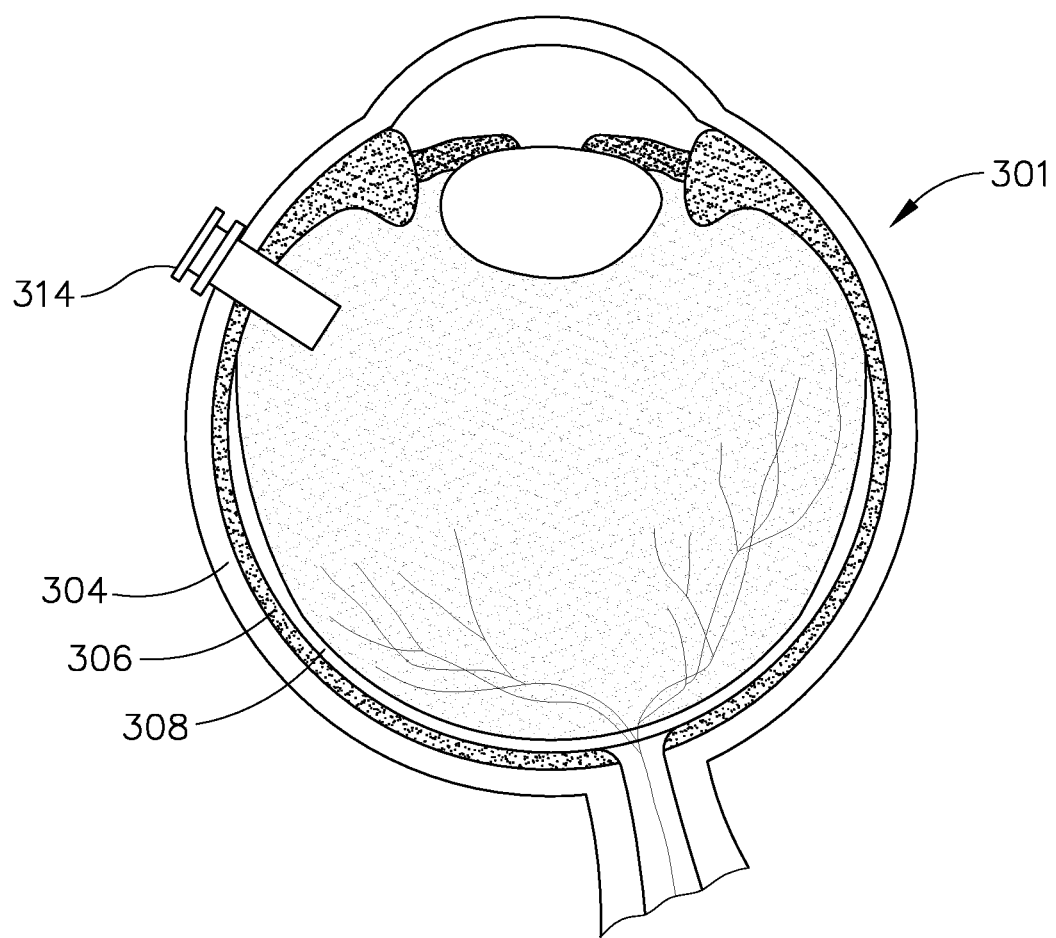
FIG. 4A depicts a cross-sectional view of an eye of a patient, with a chandelier installed in the eye.

In the present example, the procedure begins by an operator immobilizing tissue surrounding a patient's eye (301) (e.g., the eyelids) using a speculum, and/or any other instrument suitable for immobilization. While immobilization described herein with reference to tissue surrounding eye (301), it should be understood that eye (301) itself may remain free to move. Once the tissue surrounding eye (301) has been immobilized, an eye chandelier port (314) is inserted into eye (301), as shown in FIG. 4A, to provide intraocular illumination when the interior of eye (301) is viewed through the pupil. In the present example, eye chandelier port (314) is positioned in the inferior medial quadrant such that a superior temporal quadrant sclerotomy may be preformed. Eye chandelier port (314) is positioned to direct light onto the interior of eye (301) to illuminate at least a portion of the retina (e.g., including at least a portion of the macula). As will be understood, such illumination corresponds to an area of eye (301) that is being targeted for delivery of therapeutic agent.

In the present example, only chandelier port (314) is inserted at the stage shown in FIG. 4A, without yet inserting an optical fiber (315) into port (314). In some other versions, an optical fiber (315) may be inserted into chandelier port (314) at this stage. In either case, a microscope may optionally be utilized to visually inspect the eye to confirm proper positioning of eye chandelier port (314) relative to the target site. Although FIG. 4A shows a particular positioning of eye chandelier port (314), it should be understood that eye chandelier port (314) may have any other positioning as will be apparent to those of ordinary skill in the art in view of the teachings herein.

Figure 4B:
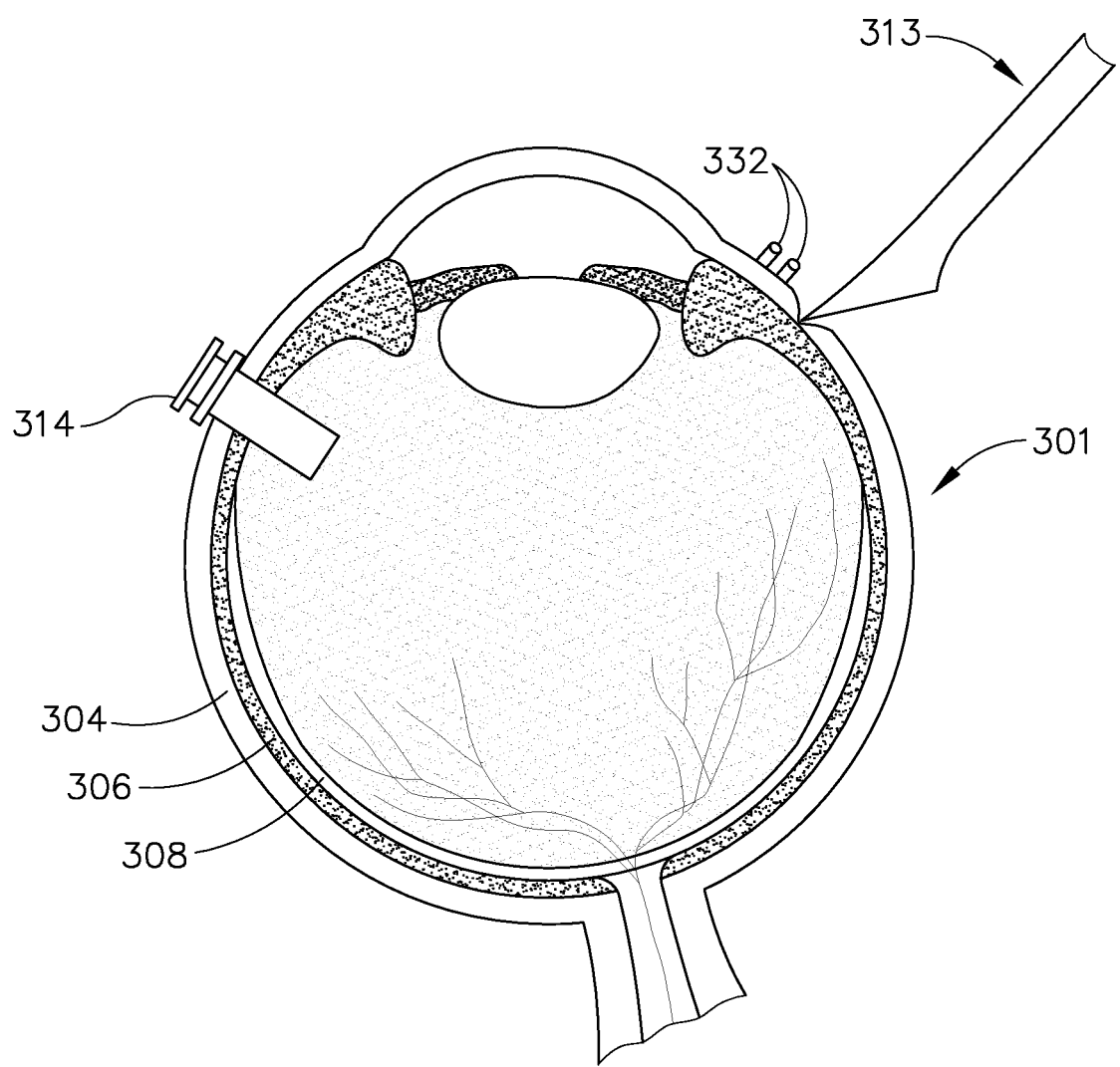
FIG. 4B depicts a cross-sectional view of the eye of FIG. 4A, with a suture loop attached to the eye, and with a sclerotomy being performed.

Once eye chandelier port (314) has been positioned, the sclera (304) may be accessed by dissecting the conjunctiva by incising a flap in the conjunctiva and pulling the flap posteriorly. After such a dissection is completed, the exposed surface (305) of the sclera (304) may optionally be blanched using a cautery tool to minimize bleeding. Once conjunctiva dissection is complete, the exposed surface (305) of the sclera (304) may optionally be dried using a WECK-CEL or other suitable absorbent device. A template may then be used to mark eye (301), as described in U.S. Pub. No. 2015/0223977, entitled "Method and Apparatus for Subretinal Administration of Therapeutic Agent," published Aug. 13, 2015, the disclosure of which is incorporated by reference herein. An operator may then use a visual guide created using the template to attach a suture loop assembly (332) and to perform a sclerotomy, as shown in FIG. 4B, using a conventional scalpel (313) or other suitable cutting instrument. The sclerotomy procedure forms a small incision through sclera (304) of eye (301). The sclerotomy is preformed with particular care to avoid penetration of the choroid (306). Thus, the sclerotomy procedure provides access to the space between sclera (304) and choroid (306). Once the incision is made in eye (301), a blunt dissection may optionally be performed to locally separate sclera (304) from choroid (306). Such a dissection may be performed using a small blunt elongate instrument, as will be apparent to those of ordinary skill in the art in view of the teachings herein.

Figure 4C:
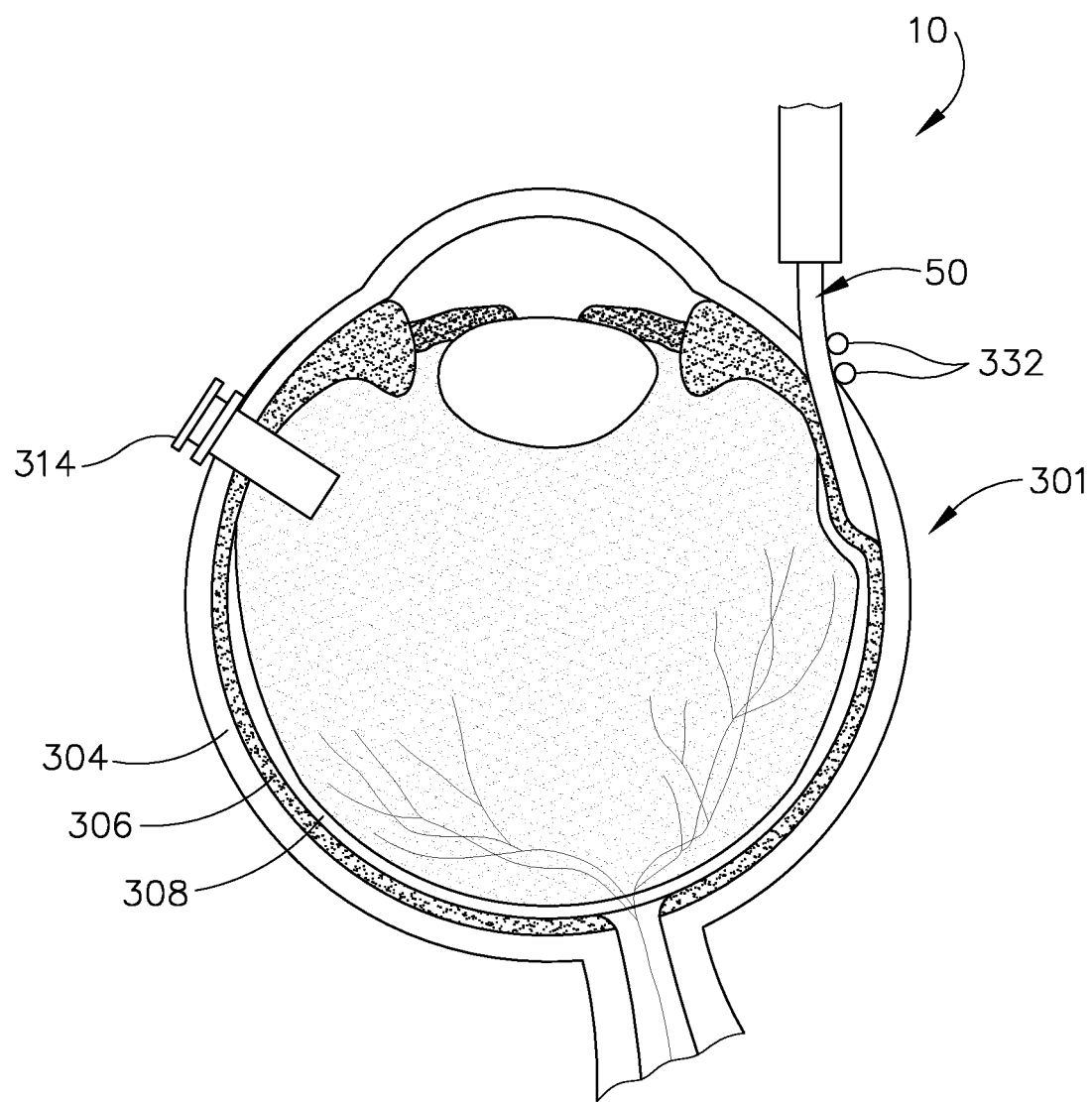
FIG. 4C depicts a cross-sectional view of the eye of FIG. 4A, with the instrument of FIG. 1 being inserted through the sclerotomy opening and in between the sclera and choroid of the eye.

With the sclerotomy procedure performed, an operator may insert cannula (50) of instrument (10) through incision (316) and into the space between sclera (304) and choroid (306). As can be seen in FIG. 4C, cannula (50) is directed through suture loop assembly (332) and into the incision. Suture loop assembly (332) may stabilize cannula (50) during insertion. Additionally, suture loop assembly (332) maintains cannula (50) in a generally tangential orientation relative to the incision. Such tangential orientation may reduce trauma as cannula (50) is guided through the incision. As cannula (50) is inserted into the incision through suture loop assembly (332), an operator may use forceps or other instruments to further guide cannula (50) along an atraumatic path. Of course, use of forceps or other instruments is merely optional, and may be omitted in some examples.

Although not shown, it should be understood that in some examples cannula (50) may include one or more markers on the surface of cannula (50) to indicate various depths of insertion. While merely optional, such markers may be desirable to aid an operator in identifying the proper depth of insertion as cannula (50) is guided along an atraumatic path. For instance, the operator may visually observe the position of such markers in relation to suture loop assembly (332) and/or in relation to the incision in the sclera (304) as an indication of the depth to which cannula (50) is inserted in eye (301). By way of example only, one such marker may correspond to an approximately 6 mm depth of insertion of cannula (50).

Figure 4D:
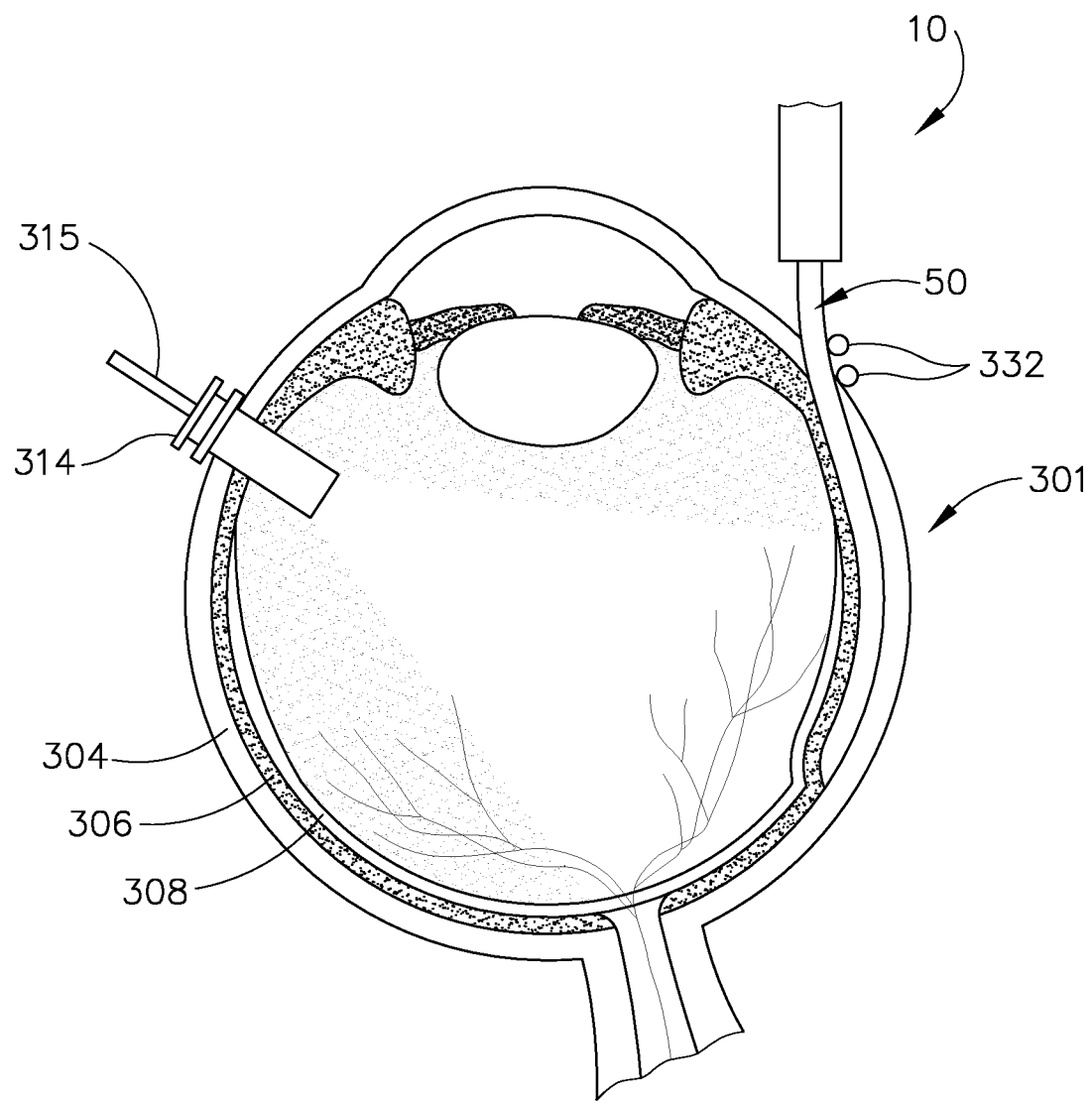
FIG. 4D depicts a cross-sectional view of the eye of FIG. 4A, with the instrument of FIG. 1 under direct visualization at the back of the eye, between the sclera and choroid.

As shown in FIG. 4D, once cannula (50) is at least partially inserted into eye (301), an operator may insert an optical fiber (315) into eye chandelier port (314) if the fiber (315) had not yet been inserted at this stage. With eye chandelier port (314) in place and assembled with optical fiber (315), an operator may activate eye chandelier port (314) by directing light through optical fiber (315) to provide illumination of eye (301) and thereby visualize the interior of eye (301). Further adjustments to the positioning of cannula (50) may optionally be made at this point to ensure proper positioning relative to the area of geographic atrophy of retina (308). In some instances, the operator may wish to rotate the eye (301), such as by pulling on suture loop assembly (332), to direct the pupil of the eye (301) toward the operator in order to optimize visualization of the interior of the eye (301) via the pupil.

FIGS. 4C-4D show cannula (50) as it is guided between sclera (304) and choroid (306) to the delivery site for the therapeutic agent. In the present example, the delivery site corresponds to a generally posterior region of eye (301) adjacent to an area of geographic atrophy of retina (308). In particular, the delivery site of the present example is superior to the macula, in the potential space between the neurosensory retina and the retinal pigment epithelium layer. By way of example only, the operator may rely on direct visualization through a microscope directed through the pupil of eye (301) as cannula (50) is being advanced through the range of motion shown in FIGS. 4C-4D, with illumination provided through fiber (315) and port (314). Cannula (50) may be at least partially visible through a retina (308) and choroid (306) of eye (301). Visual tracking may be enhanced in versions where an optical fiber is used to emit visible light through the distal end of cannula (50).

Figure 4E:
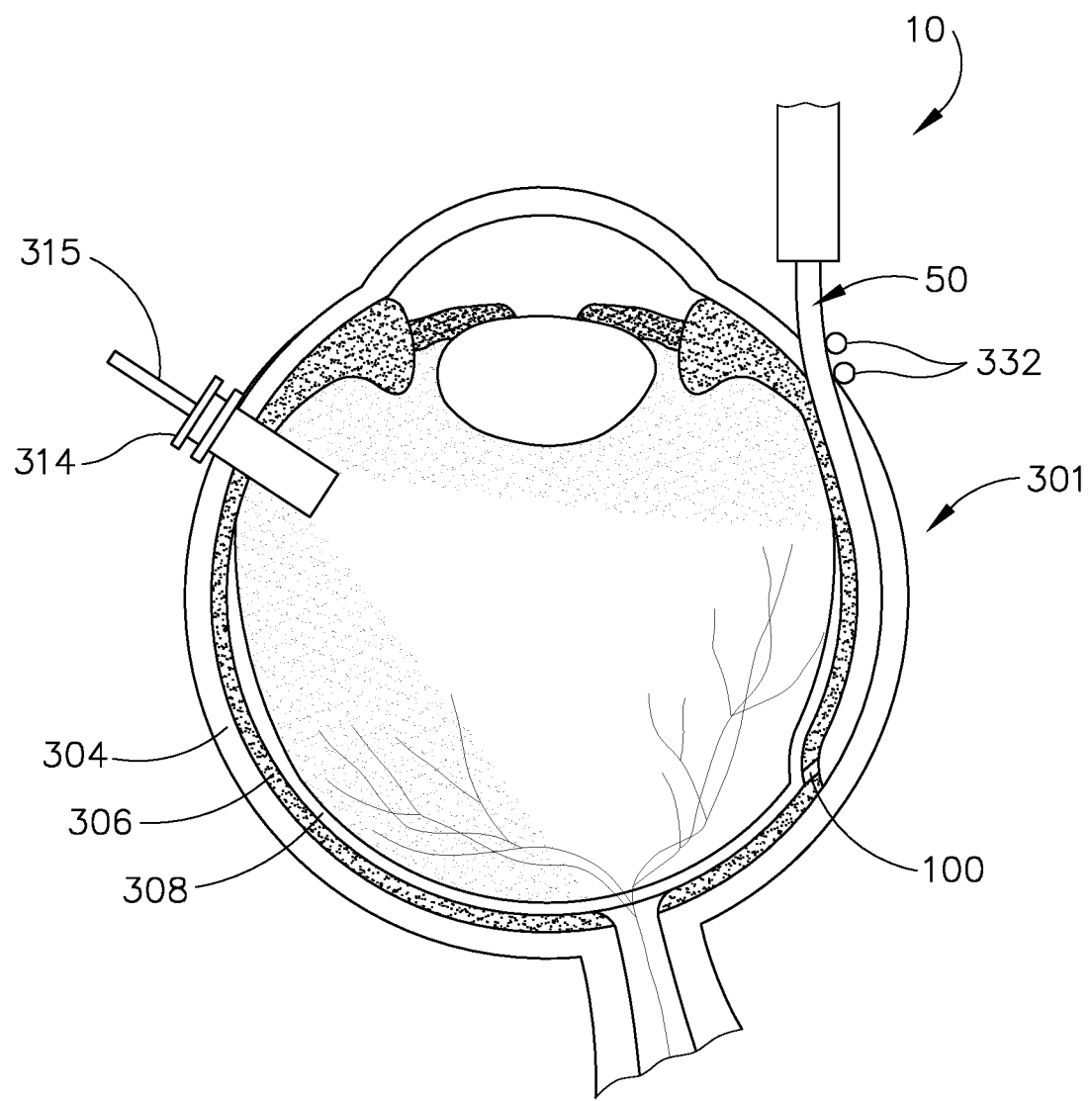
FIG. 4E depicts a cross-sectional view of the eye of FIG. 4A, with the needle of the instrument of FIG. 1 being advanced under direct visualization at the back of the eye, pressing against the outer surface of the choroid causing the choroid to "tent"
Figure 5A:
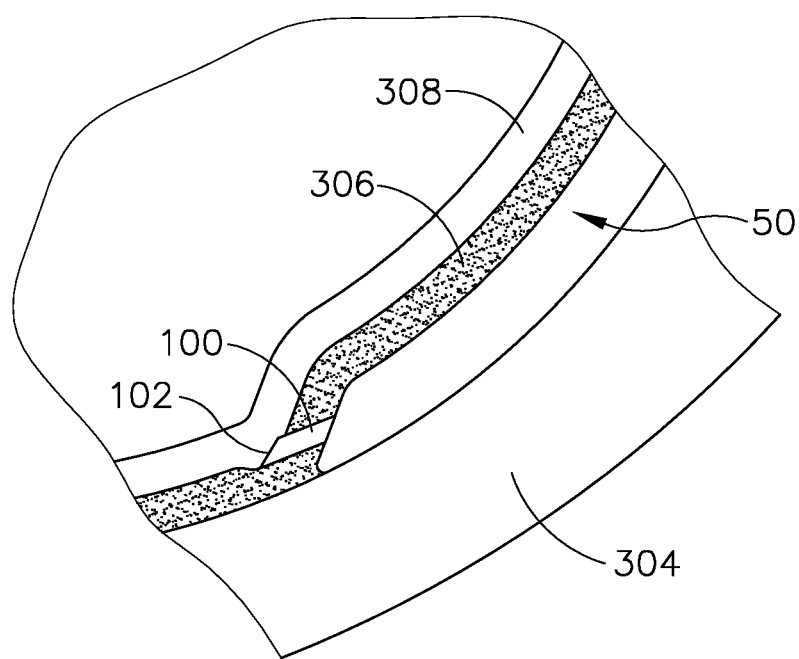
FIG. 5A depicts a detailed cross-sectional view of the eye of FIG. 4A depicted in the state shown in FIG. 4E.

Once cannula (50) has been advanced to the delivery site as shown in FIG. 4D, an operator may advance needle (100) of instrument (10) as described above by actuating knob (26). As can be seen in FIGS. 4E and 5A, needle (100) is advanced relative to cannula (50) such that needle (100) pierces through choroid (306) without penetrating retina (308). Immediately prior to penetrating choroid (306), needle (100) may appear under direct visualization as "tenting" the surface of choroid (306). In other words, needle (100) may deform choroid (306) by pushing upwardly on choroid (306), providing an appearance similar to a tent pole deforming the roof of a tent. Such a visual phenomenon may be used by an operator to identify whether choroid (306) is about to be pierced and the location of any eventual piercing. The particular amount of needle (100) advancement sufficient to initiate "tenting" and subsequent piercing of choroid (306) may be of any suitable amount as may be determined by a number of factors such as, but not limited to, general patient anatomy, local patient anatomy, operator preference, and/or other factors. As described above, a merely exemplary range of needle (100) advancement may be between approximately 0.25 mm and approximately 10 mm; or more particularly between approximately 2 mm and approximately 6 mm.

Figure 4F:
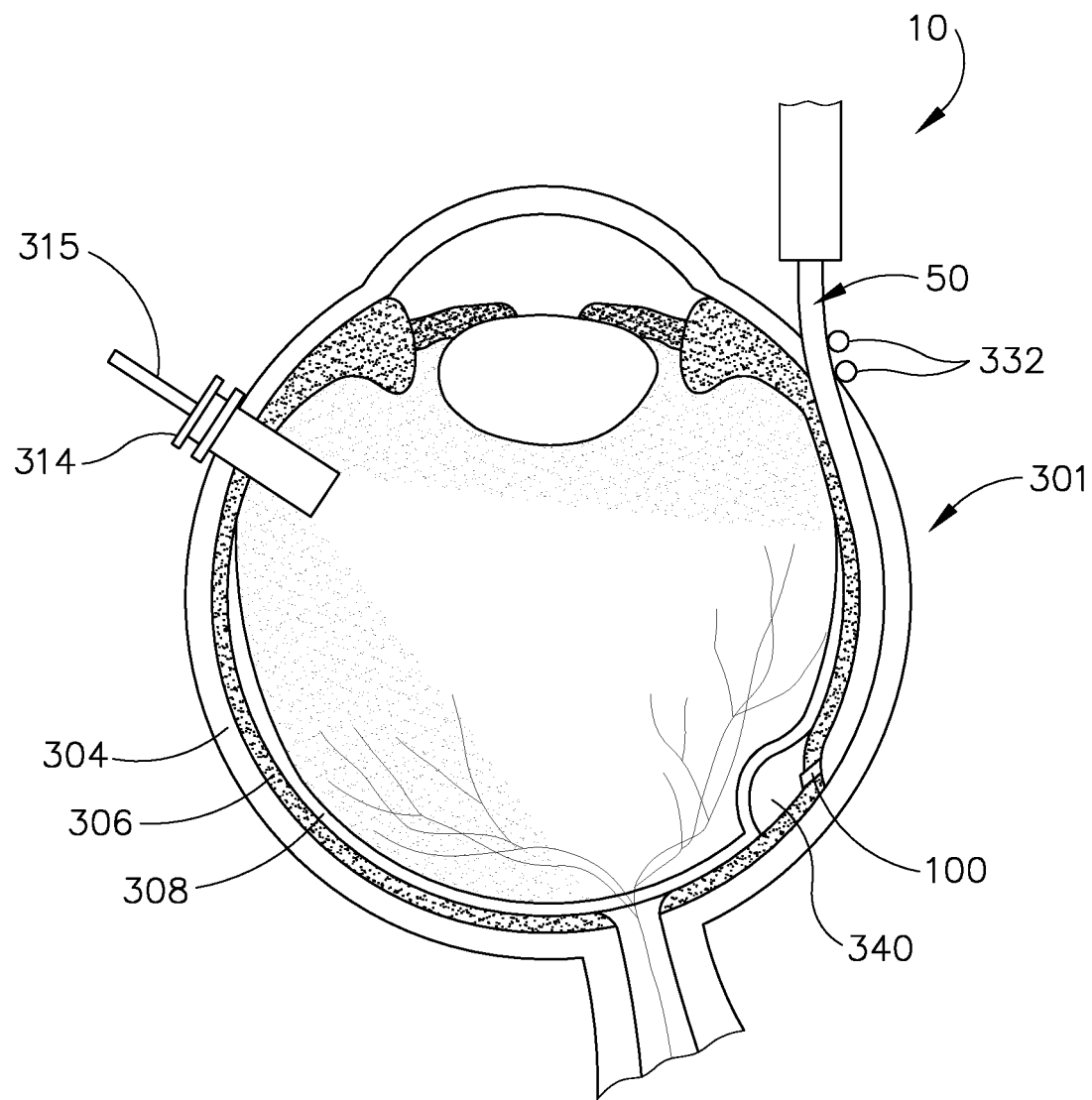
FIG. 4F depicts a cross-sectional view of the eye of FIG. 4A, with the needle dispensing a leading bleb under direct visualization at the back of the eye, the needle between the sclera and choroid, and the leading bleb in the sub retinal space between the choroid and a retina.
Figure 5B:
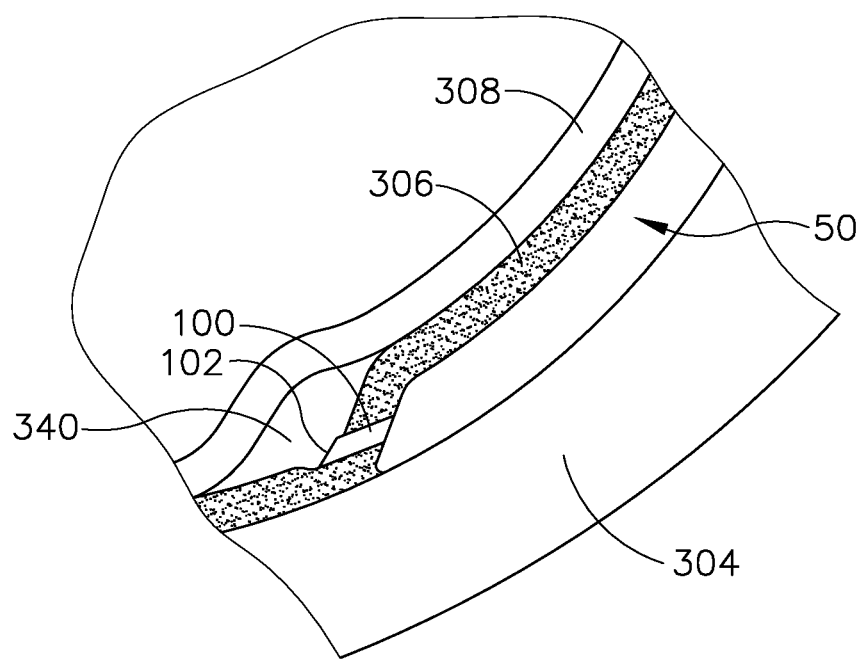
FIG. 5B depicts a detailed cross-sectional view of the eye of FIG. 4A depicted in the state shown in FIG. 4F.

In the present example, after the operator has confirmed that needle (100) has been properly advanced by visualizing the tenting effect described above, the operator infuses a balanced salt solution (BSS) or other similar solution as needle (100) is advanced relative to cannula (50). Such a BSS may form a leading bleb (340) ahead of needle (100) as needle (100) is advanced through choroid (306). Leading bleb (340) may be desirable for two reasons. First, as shown in FIGS. 4F and 5B, leading bleb (340) may provide a further visual indicator to an operator to indicate when needle (100) is properly positioned at the delivery site. Second, leading bleb (340) may provide a barrier between needle (100) and retina (308) once needle (100) has penetrated choroid (306). Such a barrier may push the retinal wall outwardly, thereby minimizing the risk of retinal perforation as needle (100) is advanced to the delivery site. In some versions, a foot pedal is actuated in order to drive leading bleb (340) out from needle (100). Alternatively, other suitable features that may be used to drive leading bleb (340) out from needle (100) will be apparent to those of ordinary skill in the art in view of the teachings herein.

Once the operator visualizes leading bleb (340), the operator may cease infusion of BSS, leaving a pocket of fluid as can be seen in FIGS. 4F and 5B. Next, a therapeutic agent (341) may be infused by actuating a syringe or other fluid delivery device as described in various references cited herein. The particular therapeutic agent (341) delivered may be any suitable therapeutic agent configured to treat an ocular condition. Some merely exemplary suitable therapeutic agents may include, but are not necessarily limited to, drugs having smaller or large molecules, therapeutic cell solutions, certain gene therapy solutions, tissue plasminogen activators, and/or any other suitable therapeutic agent as will be apparent to those of ordinary skill in the art in view of the teachings herein. By way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. In addition to, or as an alternative to, being used to deliver a therapeutic agent (341), instrument (10) and variations thereof may be used to provide drainage and/or perform other operations.

Figure 4G:
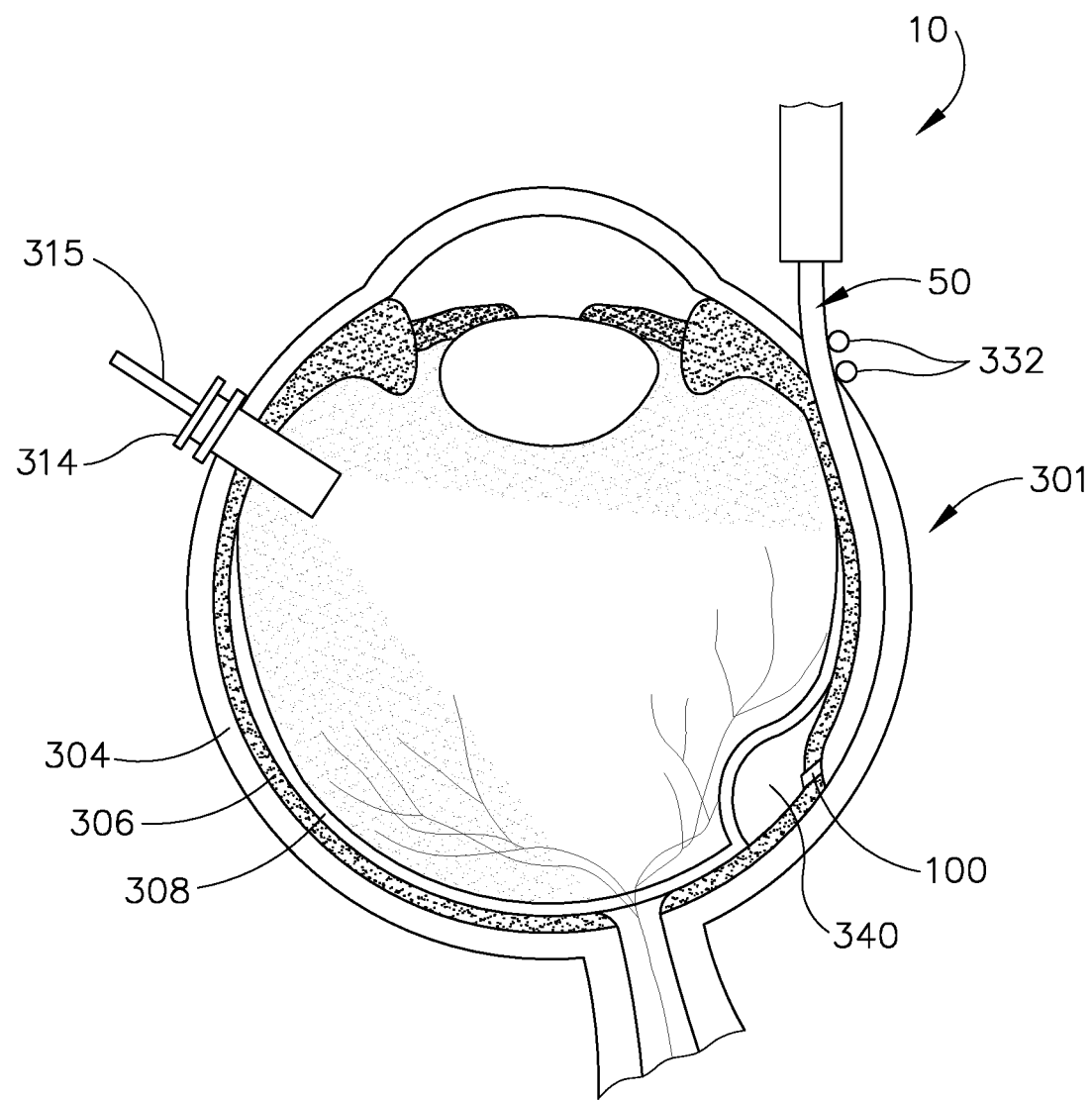
FIG. 4G depicts a cross-sectional view of the eye of FIG. 4A, with the needle dispensing a therapeutic agent to the eye at the back of the eye, between the sclera and choroid.
Figure 5C:
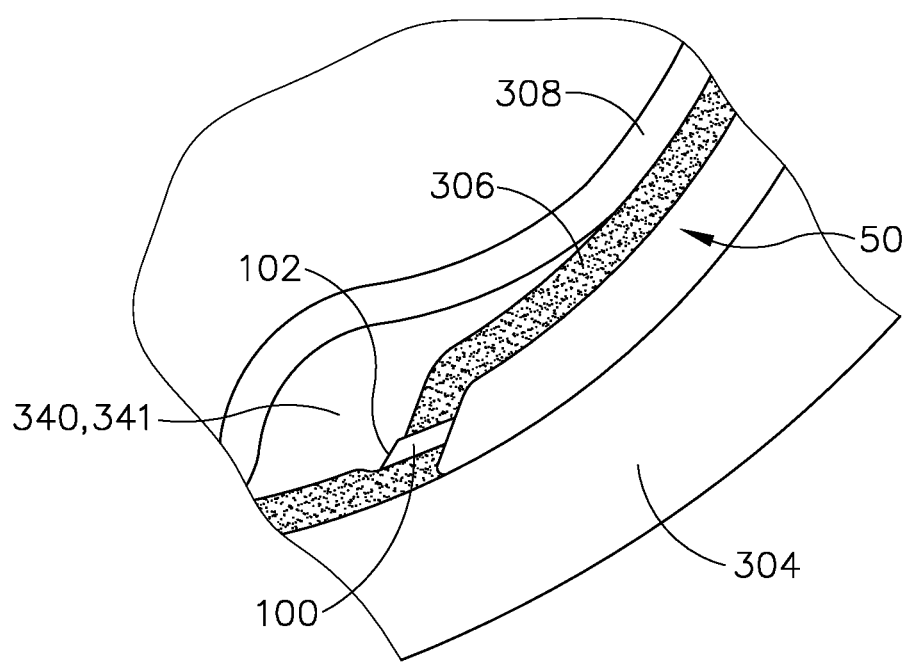
FIG. 5C depicts a detailed cross-sectional view of the eye of FIG. 4A depicted in the state shown in FIG. 4G.

In the present example, the amount of therapeutic agent (341) that is ultimately delivered to the delivery site is approximately 50 µL, although any other suitable amount may be delivered. In some versions, a foot pedal is actuated in order to drive agent (341) out from needle (100). Alternatively, other suitable features that may be used to drive agent (341) out from needle (100) will be apparent to those of ordinary skill in the art in view of the teachings herein. Delivery of therapeutic agent (341) may be visualized by an expansion of the pocket of fluid as can be seen in FIGS. 4G and 5C. As shown, therapeutic agent (341) essentially mixes with the fluid of leading bleb (340) as therapeutic agent (341) is injected into the suprachoroidal, subretinal space.

Once delivery is complete, needle (100) may be retracted by rotating knob (26) in a direction opposite to that used to advance needle (100); and cannula (50) may then be withdrawn from eye (301). It should be understood that because of the size of needle (100), the site where needle (100) penetrated through choroid (306) is self sealing, such that no further steps need be taken to seal the delivery site through choroid (306). Suture loop assembly (332) and chandelier (314) may be removed, and the incision in the sclera (304) may be closed using any suitable conventional techniques.

As noted above, the foregoing procedure may be carried out to treat a patient having macular degeneration. In some such instances, the therapeutic agent (341) that is delivered by needle (100) may comprise cells that are derived from postpartum umbilicus and placenta. As noted above, and by way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. Alternatively, needle (100) may be used to deliver any other suitable substance or substances, in addition to or in lieu of those described in U.S. Pat. No. 7,413,734 and/or elsewhere herein. By way of example only, therapeutic agent (341) may comprise various kinds of drugs including but not limited to small molecules, large molecules, cells, and/or gene therapies. It should also be understood that macular degeneration is just one merely illustrative example of a condition that may be treated through the procedure described herein. Other biological conditions that may be addressed using the instruments and procedures described herein will be apparent to those of ordinary skill in the art.

It should also be understood that the procedure described above may be carried out in accordance with any of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2015/0351958, entitled "Therapeutic Agent Delivery Device with Convergent Lumen," published Dec. 10, 2015, the disclosure of which is incorporated by reference herein; U.S. Pub. No. 2015/0351959, entitled "Sub-Retinal Tangential Needle Catheter Guide and Introducer," published Dec. 10, 2015, the disclosure of which is incorporated by reference herein; U.S. Pub. No. 2016/0074212, entitled "Method and Apparatus for Sensing Position Between Layers of an Eye," published Mar. 17, 2016, the disclosure of which is incorporated by reference herein; U.S. Pub. No. 2016/0074217, entitled "Motorized Suprachoroidal Injection of Therapeutic Agent," published Mar. 17, 2016, the disclosure of which is incorporated by reference herein; U.S. Pub. No. 2016/0074211, entitled "Therapeutic Agent Delivery Device with Advanceable Cannula and Needle," published Mar. 17, 2016, the disclosure of which is incorporated by reference herein; and/or U.S. Pub. No. 2016/0081849, entitled "Therapeutic Agent Delivery Device," published Mar. 24, 2016, the disclosure of which is incorporated by reference herein.

III. EXEMPLARY ALTERNATIVE NEEDLE FOR INSTRUMENT

Several variables may affect the relationship between the exit angle (EA) of needle (100) and the choroid (306) of any given patient. It should be understood that the choroid (306) and the retina (308) are very thin and have relatively little structural integrity. Thus, even when a very flexible cannula (50) is used, cannula (50) may tend to provide substantial separation between the choroid (306) and the sclera (304) as cannula (50) is inserted between the choroid (306) and the sclera (304). The degree of separation may vary from patient to patient (e.g., based on normal anatomical variation and/or based on the patient's disease state, etc.). In cases where the separation is truly substantial, the exit angle (EA) of needle (100) may be insufficient to result in distal tip (102) passing fully through the choroid (306). In other words, needle (100) may continue through the suprachoroidal space without fully penetrating the choroid (306).

Figure 6:
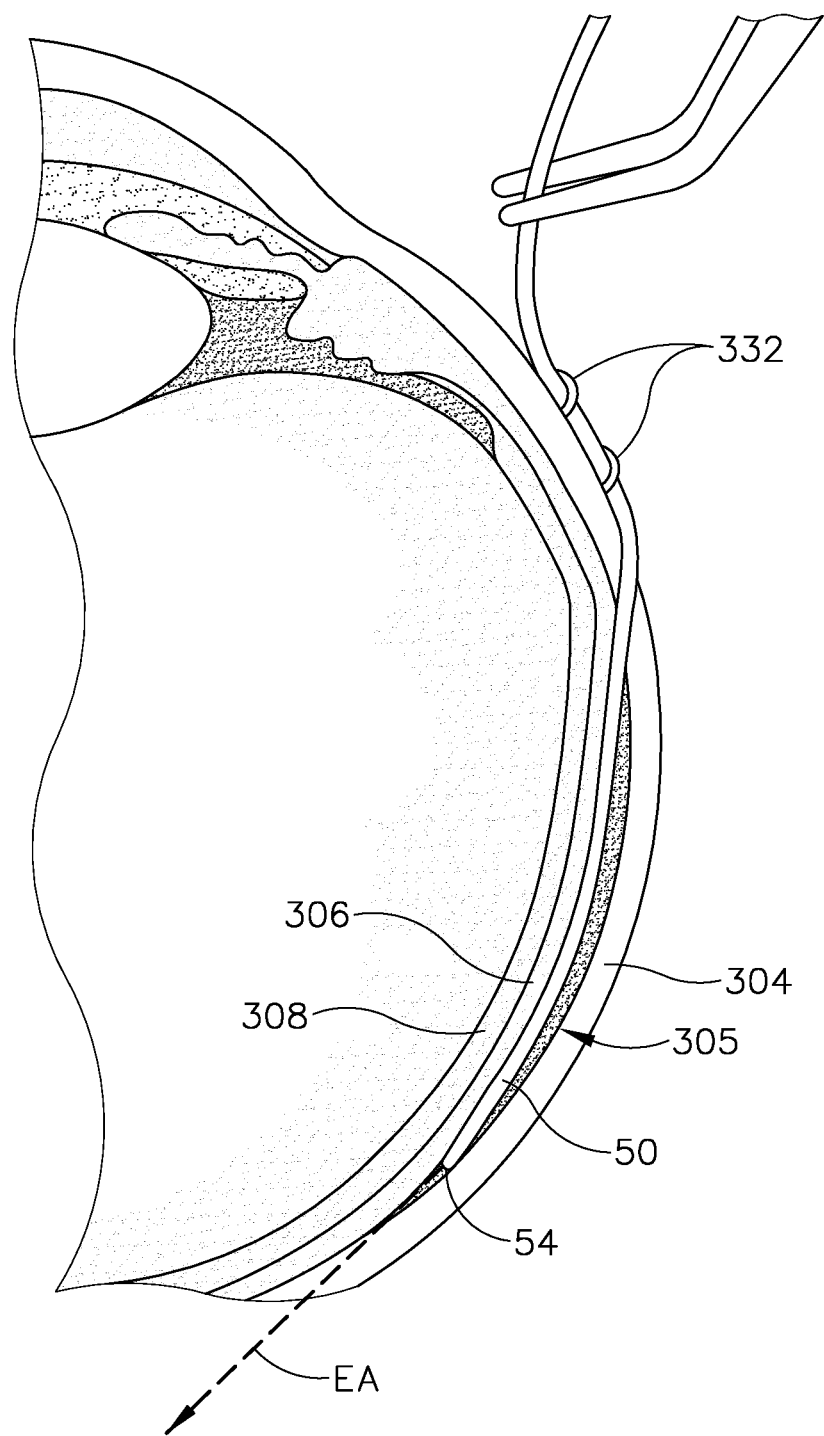
FIG. 6 depicts a cross-sectional view of the eye of FIG. 4A, with the instrument of FIG. 1 at the back of the eye, between the sclera and choroid, with the cannula of the instrument providing substantial separation between the sclera and the choroid.
Figure 7:
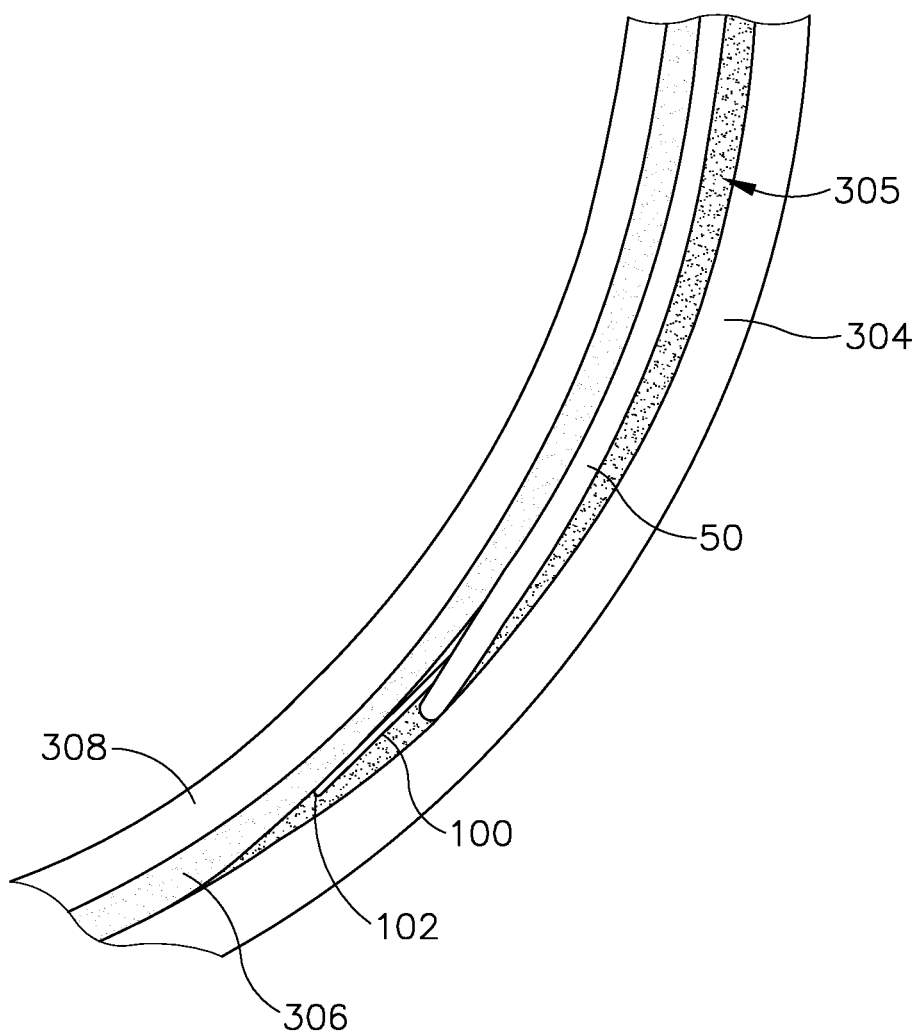
FIG. 7 depicts an enlarged view of the distal end of the cannula of the instrument of FIG. 1 at the back of the eye, between the sclera and choroid, with the cannula of the instrument providing substantial separation between the sclera and the choroid, with the needle of the instrument advanced to a distal position.

FIG. 6 shows an exemplary scenario where cannula (50) has elevated the choroid (306) and retina (308) away from the sclera (304) to the point where a substantial gap (305) is defined between the sclera (304) and the choroid (306). As also shown in FIG. 6, the exit angle (EA) is oriented such that needle (100) would not penetrate the choroid (306); and further such that needle (100) would eventually engage the sclera (304). FIG. 7 shows needle (100) advanced distally along this exit angle (EA). As shown, needle (100) passes tangentially along the choroid (306) without ever breaching the choroid (306). In some other instances, needle (100) may pass partially through the choroid (306) and immediately exit the choroid (306) without ever reaching the subretinal space between the choroid (306) and the retina (308).

If the operator determines (e.g., based on the absence of a choroidal "tenting" observation as described above) that needle (100) has not fully penetrated the choroid (306) despite needle (100) being advanced fully distally, the operator may retract needle (100) proximally, slightly reposition cannula (50) and/or another portion of instrument (10) in order to provide a better orientation for the exit angle (EA), and then try advancing needle (100) distally again. Even with such efforts, it may still be very difficult or even impossible in some cases to successfully penetrate the choroid (306) with needle (100). Even in cases where efforts to reposition are successful, the success rate may be highly dependent on the skill of the operator, and the repositioning efforts will add time to the procedure. Moreover, the repositioning may increase the risk of tissue trauma, increase the risk of bleb collapse, and/or increase the risk of cell egress into the suprachoroidal space.

It may seem apparent to address the above-noted issues by simply modifying needle guide (60) to provide a steeper exit angle (EA). However, this kind of modification may be unsuitable for many patients. In particular, increasing the exit angle (EA) by providing a more pronounced bend in distal end (62) of needle guide (60) may increase the risk of needle (100) perforating the retina (308) in some patients, particularly in those where the gap (305) created by cannula (50) between the sclera (304) and the choroid (306) is less pronounced than the gap (305) shown in FIGS. 6-7; including cases where the gap (305) is non-existent. It may therefore be desirable to provide a more nuanced solution that provides greater consistency in penetration of the choroid (306) without substantially increasing the risk of penetration of the retina (308). Such a solution may provide better accommodation of anatomical variations across patients; accommodate variation in operator technique and expertise; and minimize the level of operator training required.

Figure 8:
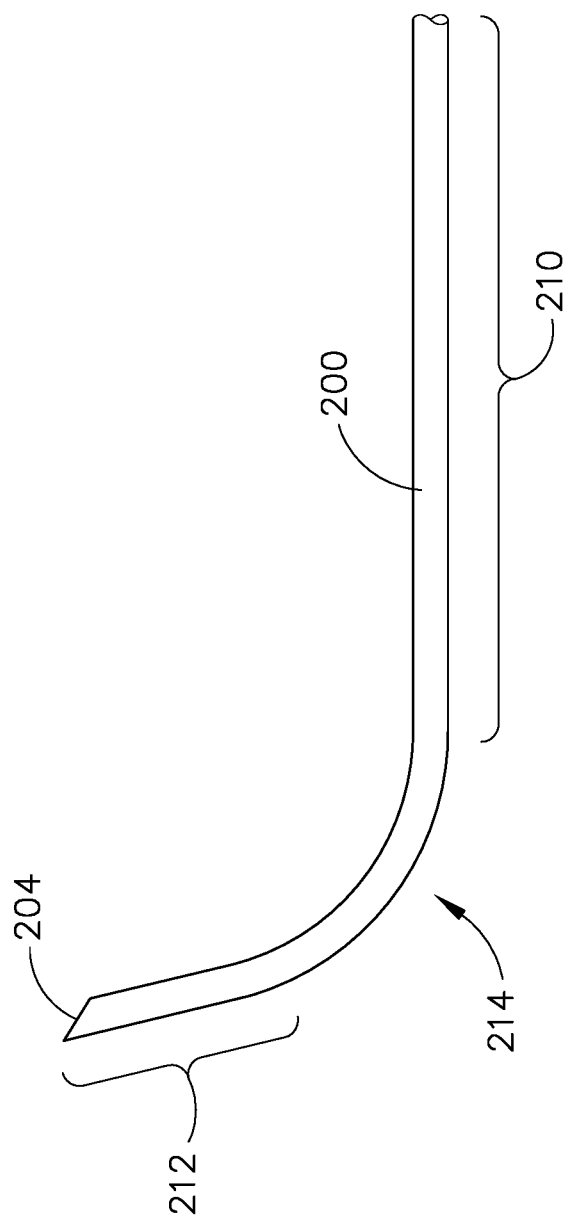
FIG. 8 depicts a side elevational view of the distal end of an exemplary alternative needle that may be incorporated into the instrument of FIG. 1.
Figure 9A:
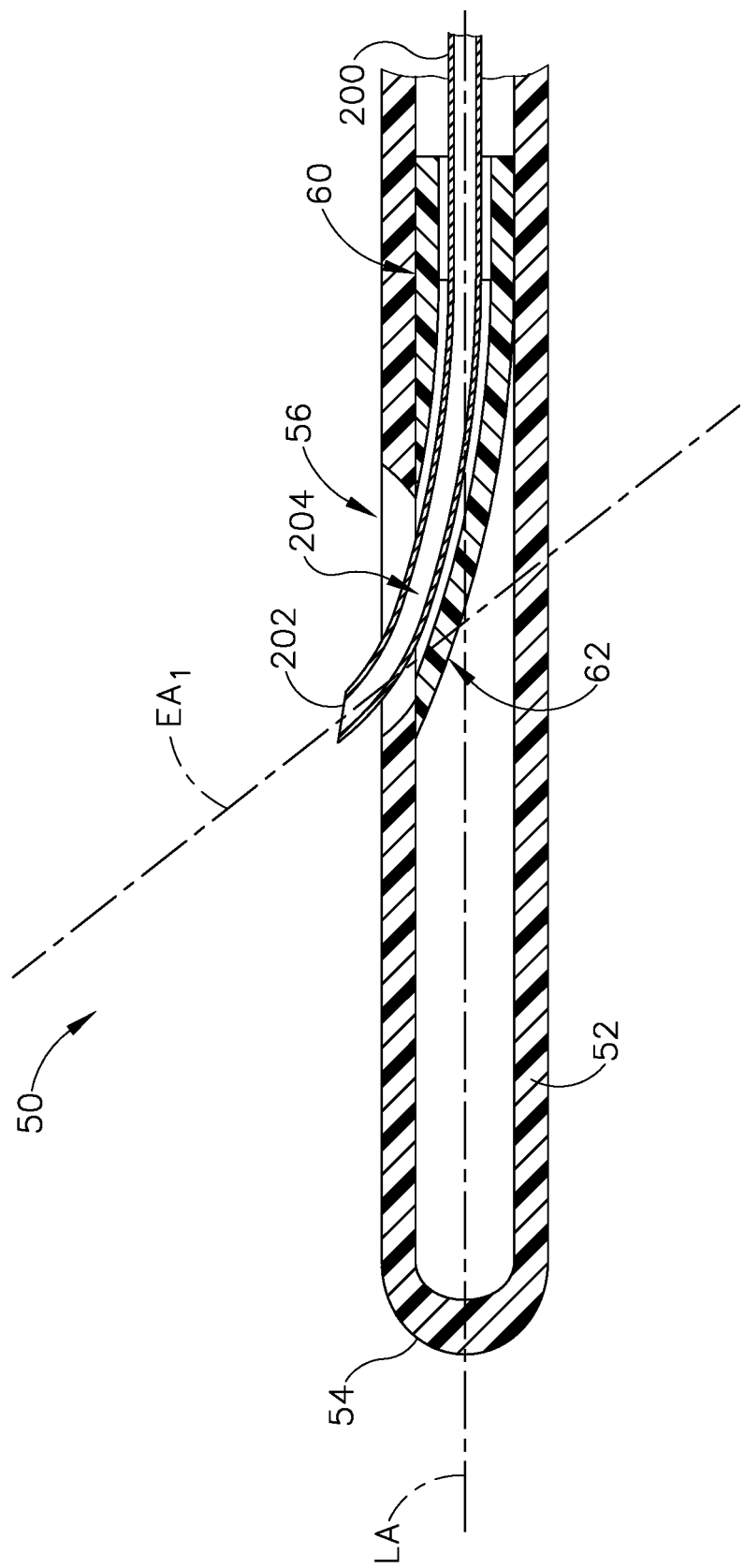
FIG. 9A depicts a cross-sectional side view of the cannula of FIG. 2, with the cross-section taken along line 3-3 of FIG. 2, with the needle of FIG. 8 in a first longitudinal position.
Figure 9B:
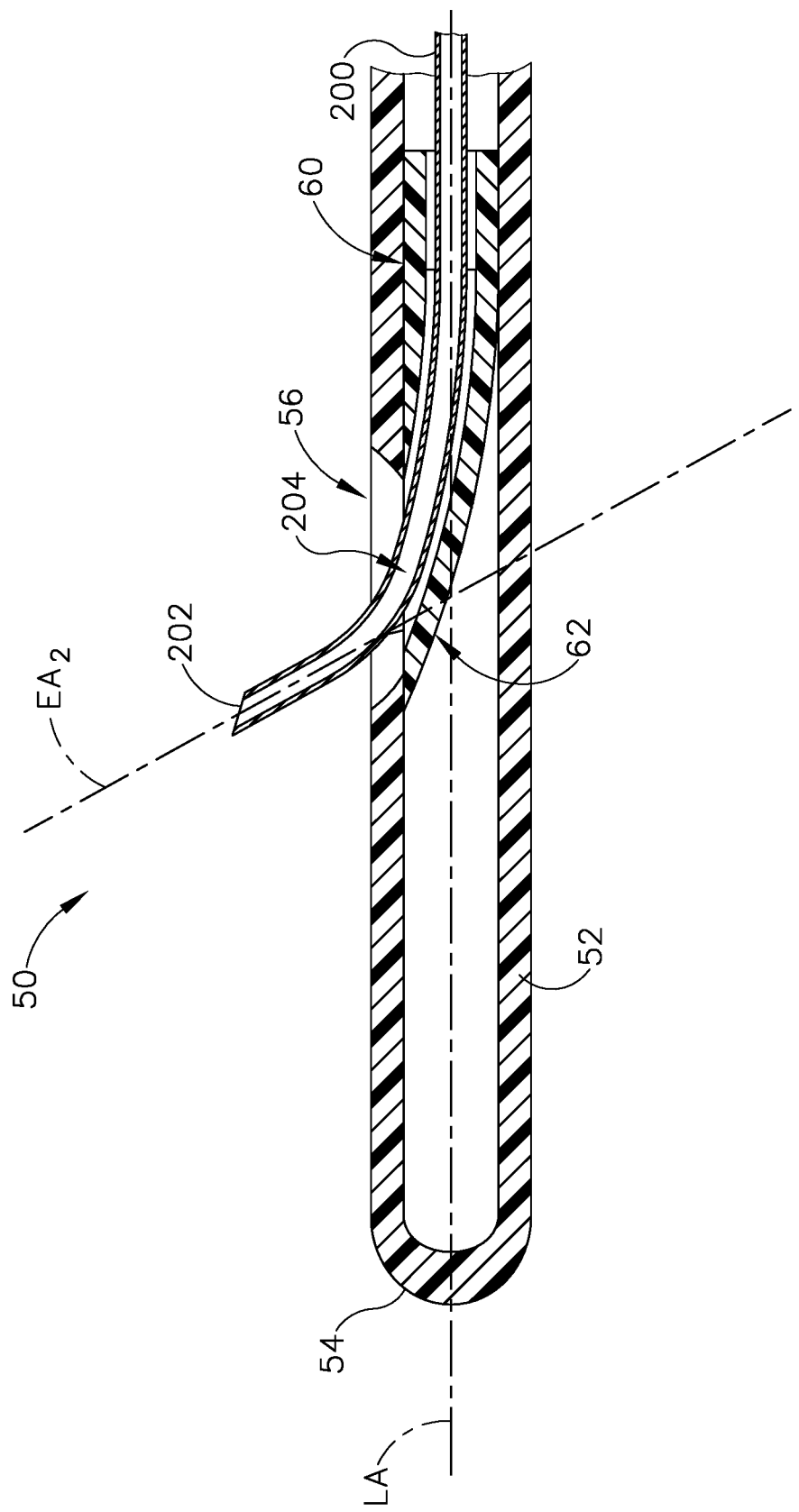
FIG. 9B depicts a cross-sectional side view of the cannula of FIG. 2, with the cross-section taken along line 3-3 of FIG. 2, with the needle of FIG. 8 in a second longitudinal position.
Figure 9C:
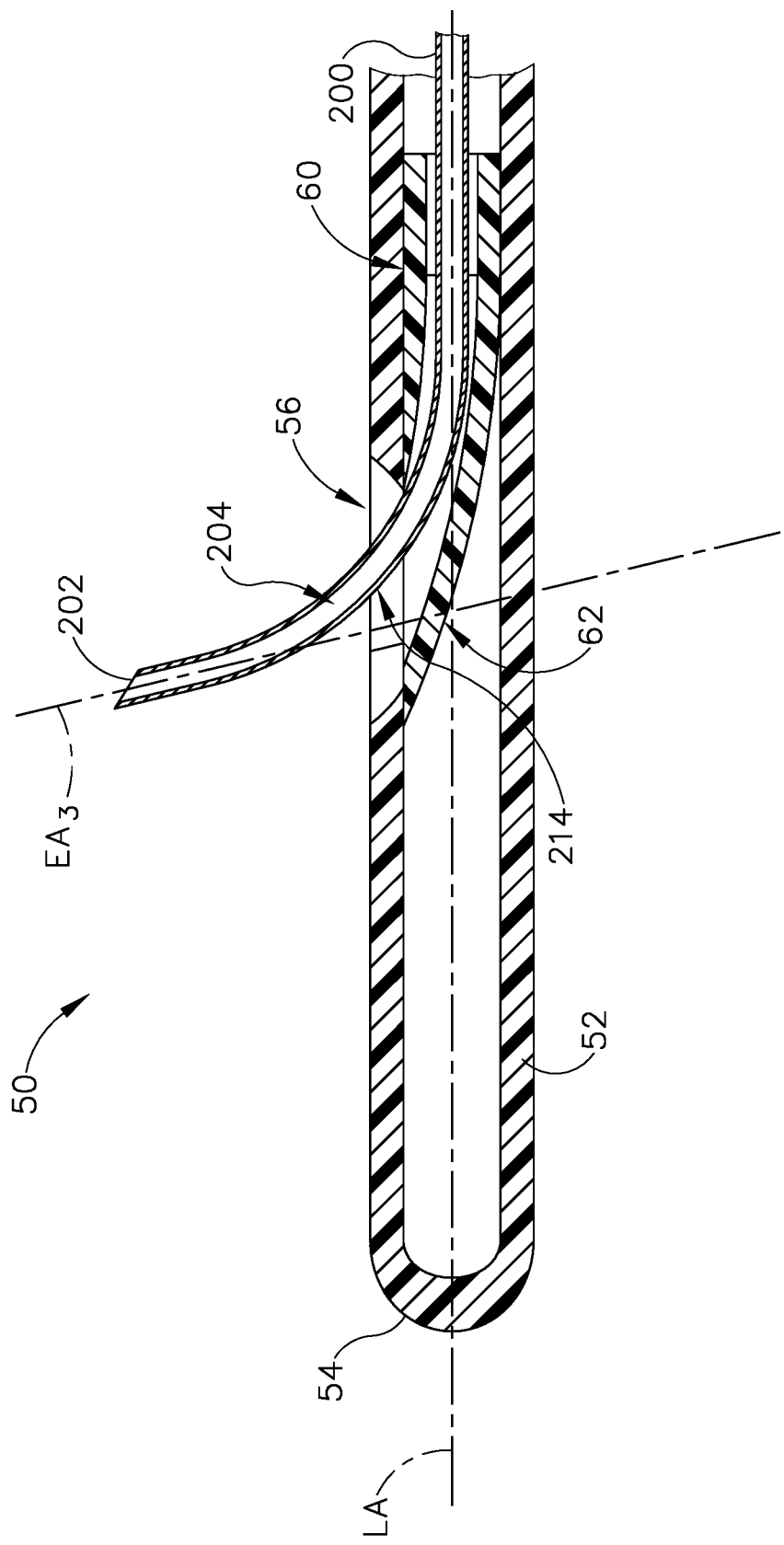
FIG. 9C depicts a cross-sectional side view of the cannula of FIG. 2, with the cross-section taken along line 3-3 of FIG. 2, with the needle of FIG. 8 in a third longitudinal position.

FIG. 8 shows an exemplary alternative needle (200) that may be incorporated into instrument (10) in place of needle (100). In some instances, needle (200) may be substituted for needle (100) without modifying any other aspects of instrument (10). Needle (200) of the present example has a distal tip (202) that is configured and operable just like distal tip (102) described above. As shown in FIGS. 9A-9C, needle (200) also defines a lumen (204) that is configured and operable just like lumen (104) described above. Unlike needle (100), however, needle (200) of the present example includes a substantially straight proximal portion (210), a substantially straight distal portion (212), and a bent portion (214) located between proximal and distal portions (210, 212). In the present example, needle (200) is formed of nitinol, though it should be understood that any other suitable material(s) (e.g., stainless steel, etc.) may be used.

Needle (200) is configured to provide bent portion (214) as a preformed feature, such that needle (200) is resiliently biased to assume the configuration shown in FIG. 6. By way of example only, bent portion (214) may be configured to have a constant radius of curvature between approximately 4 mm and approximately 15 mm; a constant radius of curvature between approximately 7 mm and approximately 12 mm; a constant radius of curvature between approximately 8 mm and approximately 11 mm; or a constant radius of curvature between approximately 9 mm and approximately 10 mm. In some versions, bent portion (214) has a radius of curvature of approximately 10.5 mm. In some other versions, bent portion (214) has a radius of curvature of approximately 10.0 mm. In some other versions, bent portion (214) has a radius of curvature of approximately 9.5 mm. It should be understood that the radius of curvature must be carefully selected because if the radius is too small, there may be an increased risk of perforating the retina (308); and if the radius is too large, the needle (200) may still fail to fully penetrate the choroid (306).

While the radius of curvature of bent portion (214) is constant in the present example, in some other versions the radius of curvature may be variable. For instance, some variations of needle (200) may provide a larger radius of curvature in a region of needle (200) that remains disposed in cannula (50), even when needle (200) is in a distally extended position; with a smaller radius of curvature in a region of needle (200) that extends distally from cannula (50) when needle (200) is in a distally extended position. This kind of configuration may impart a slight precurvature to cannula (50), which may further assist in cannula (50) conforming to the curved inner wall of sclera (304), which may in turn reduce the occurrence (or magnitude) of gap (305).

As shown in FIGS. 9A-9C, needle (200) is slidably disposed in needle guide (60) within cannula (50). While FIG. 9A shows needle (200) in a partially advanced state, it should be understood that needle (200) may be retracted further proximally in needle guide (60) such that distal tip (202) does not protrude through lateral opening (56). As shown in FIG. 9A, as needle (200) begins to exit cannula (50) via lateral opening (56), the distally protruding portion of needle (200) is oriented along a first exit axis ($EA_1$). At this stage, bent portion (214) and part of distal portion (212) are still contained within needle guide (60), such that needle guide (60) prevents needle (200) from reaching the configuration shown in FIG. 8.

As the operator continues to advance needle (200) distally relative to cannula (50), more of needle (200) protrudes distally from lateral opening (56), as shown in FIG. 9B. Due to the resilient bias of needle (200), the now longer protruding portion of needle (200) is oriented along a second exit axis ($EA_2$). Second exit axis ($EA_2$) defines an angle with the longitudinal axis (LA) that is larger than the angle defined between first exit axis ($EA_1$) and the longitudinal axis (LA). As the operator continues to advance needle (200) further distally relative to cannula (50), even more of needle (200) protrudes distally from lateral opening (56), as shown in FIG. 9C. Due to the resilient bias of needle (200), the now longer protruding portion of needle (200) is oriented along a third exit axis ($EA_3$). Third exit axis ($EA_3$) defines an angle with the longitudinal axis (LA) that is larger than the angle defined between second exit axis ($EA_3$) and the longitudinal axis (LA). Thus, the further needle (200) is advanced, the larger the angle defined between the exit axis (EA) and the longitudinal axis (LA). It should be understood that the depictions of exit axes ($EA_1$, $EA_2$, $EA_3$) in FIGS. 9A-9C may be somewhat exaggerated, for illustrative purposes only.

Figure 10:
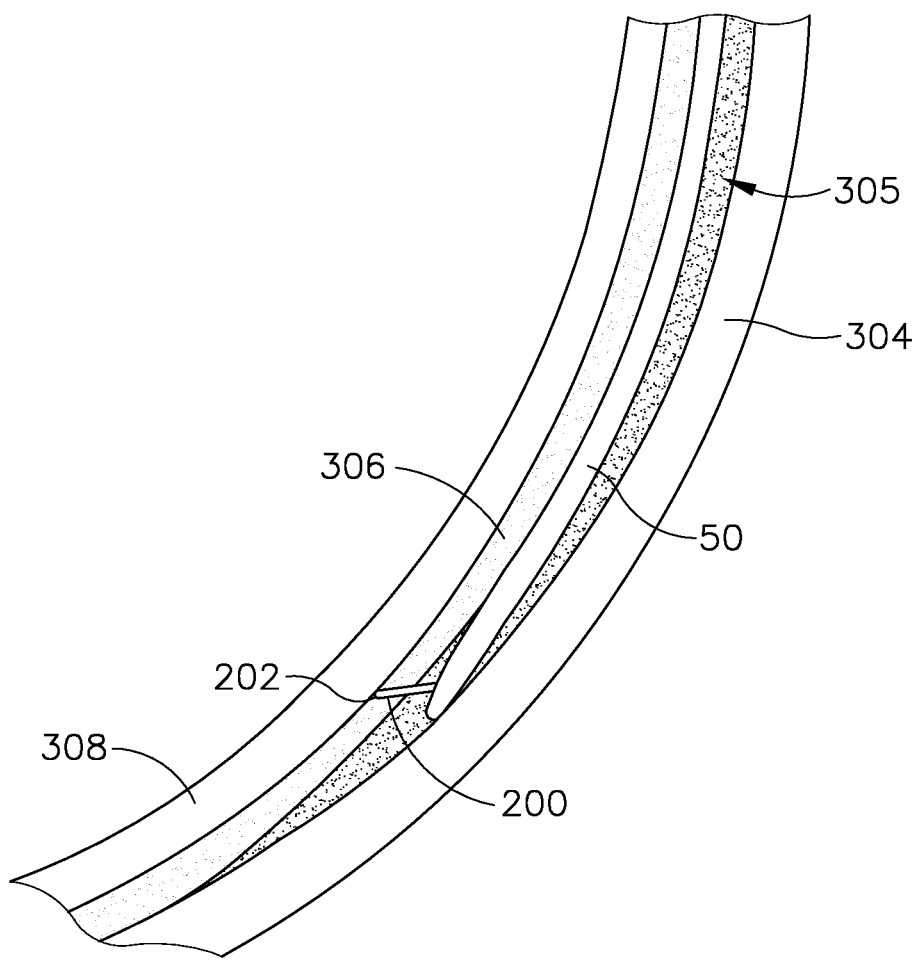
FIG. 10 depicts an enlarged view of the distal end of the cannula of the instrument of FIG. 1 at the back of the eye, between the sclera and choroid, with the needle of FIG. 8 disposed in the cannula, with the cannula of the instrument providing substantial separation between the sclera and the choroid, and with the needle of FIG. 8 advanced to a distal position.

As shown in FIG. 10, needle (200) may be particularly useful in cases where cannula creates a substantial gap (305) between the sclera (304) and the choroid (306). It should be understood that the gap (305) in FIG. 10 is substantially the same as the gap (305) in FIG. 7. As noted above, due to the gap (305) in FIG. 7 and the associated relationships between the anatomical structures and the instrument (10) structures, needle (100) is unable to penetrate choroid (306). However, as shown in FIG. 10, the curvature of needle (200) allows needle (200) to penetrate choroid (306) despite the presence of gap (305) and the associated relationships between the anatomical structures and the instrument (10) structures.

As noted above, the exit angle (EA) of needle (200) varies based on the extent to which needle (200) is extended from cannula (50). It should be understood that this variation in the exit angle (EA) will allow the operator to control the optimal exit angle (EA) by controlling the amount of needle (200) extension. This may allow for shallower angles (less extension) for some patients and steeper angles (more extension) for other patients, to more consistently be able to achieve penetration of the choroid (306) in a relatively safe and efficient manner, eliminating the need for other mitigations or workarounds that would otherwise be required from the scenario depicted in FIG. 7.

IV. EXEMPLARY CANNULA NEEDLE FOR INSTRUMENT

As noted above, cannula (50) includes a closed distal end (54) and a lateral opening (56) that is located proximal to distal end (54). In some instances, it may be desirable to provide an alternative cannula that has an open distal end, without a lateral opening. By way of example only, this may provide simplified manufacturing processes. Since it may still be desirable to have a needle exit the cannula at such that the distal tip of the needle is oriented along an axis that is oblique to the longitudinal axis of the cannula, it may be desirable to use a needle with a preformed curve in versions where the cannula has an open distal end.

Figure 11A:
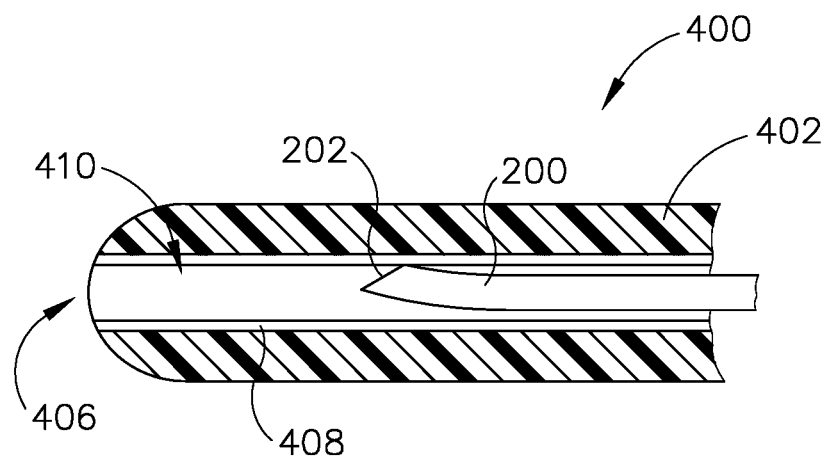
FIG. 11A depicts a cross-sectional side view of the needle of FIG. 8 disposed in an exemplary alternative cannula that may be incorporated into the instrument of FIG. 1, with the needle in a proximal position.

FIG. 11A shows an exemplary alternative cannula (400) that may be readily incorporated into instrument (10) in place of cannula (50). Cannula (400) of this example has a flexible body (402) and a distal opening (406). Distal opening (406) is coaxially positioned on the longitudinal axis of cannula (400) in this example. In some other versions, distal opening (406) is offset from the longitudinal axis of cannula (400). By way of example only, cannula (400) may be formed of Polyether block amide (PEBA) and/or any other suitable kind(s) of material(s). Like cannula (50), cannula (400) of the present example has sufficient column strength to be advanced distally between the sclera (306) and choroid (308) of patient's eye without buckling.

Figure 11B:
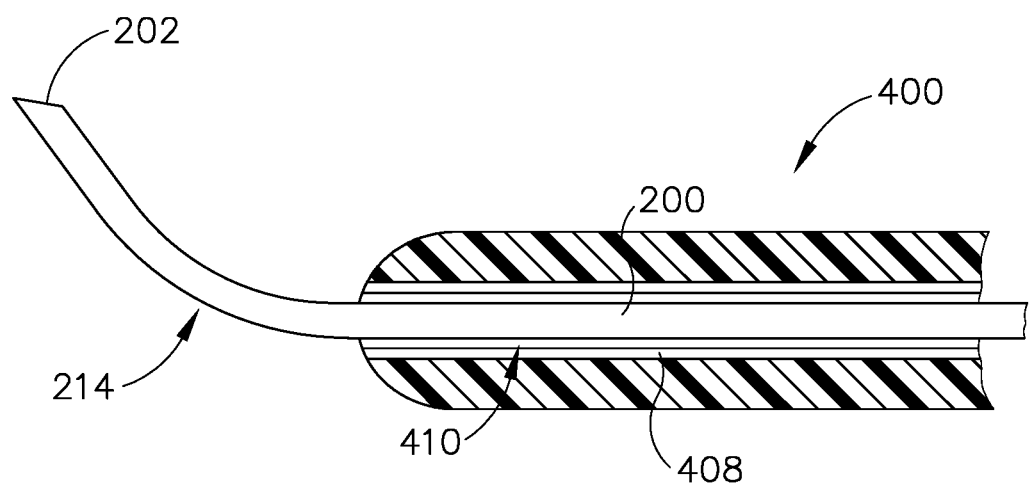
FIG. 11B depicts a cross-sectional side view of the needle of FIG. 8 disposed in the cannula of FIG. 11A, with the needle in a distal position.

An insert (408) is positioned within cannula (400). Insert (408) may be secured within cannula (400) by a press or interference fit, by adhesives, by mechanical locking mechanisms, and/or in any other suitable fashion. In the present example, insert (408) is formed of a polyimide material, though it should be understood that any other suitable biocompatible material(s) may be used. Insert (408) of the present example is substantially straight yet may bend with cannula (400). Needle (200) is slidably disposed in a lumen (410) defined by insert (408). When needle (200) is in a proximal position as shown in FIG. 11A, distal tip (202) of needle (200) is fully contained within lumen (410). At this stage, insert (408) constrains needle (200) such that needle (200) is held under stress in a substantially straight configuration. When needle (200) is in a distal position as shown in FIG. 11B, distal tip (202) of needle is positioned distally of cannula (400). At this stage, curved portion (214) is exposed such that the distal portion (212) of needle (200) is oriented along an exit axis that is oblique to the longitudinal axis of cannula (400). It should be understood that this configuration and orientation may position distal tip (202) at the subretinal space (i.e., between the choroid (306) and the retina (308)).

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body; (b) a cannula extending distally from the body, wherein the cannula is flexible; and (c) a needle slidably disposed in the cannula, wherein the needle includes: (i) a sharp distal tip, wherein the needle is configured to translate relative to the cannula between a proximal position and a distal position, wherein the distal tip is configured to be positioned inside the cannula when the needle is in the proximal position, wherein the distal tip is configured to be positioned outside the cannula when the needle is in the distal position, and (ii) a curved portion, wherein the needle is resiliently biased to extend along a curve through the curved portion.

Example 2

The apparatus of Example 1, wherein the cannula includes: (i) a closed distal end, and (ii) a lateral opening located proximal to the closed distal end.

Example 3

The apparatus of Example 2, wherein the cannula further includes a ramp feature, wherein the ramp feature extends from an interior region of the cannula to the lateral opening.

Example 4

The apparatus of any one or more of Examples 1 through 3, wherein the curved portion is resiliently biased to define a constant radius of curvature.

Example 5

The apparatus of Example 4, wherein the radius of curvature is between approximately 7 mm and approximately 12 mm.

Example 6

The apparatus of Example 4, wherein the radius of curvature is between approximately 4 mm and approximately 15 mm.

Example 7

The apparatus of Example 4, wherein the radius of curvature is between approximately 9 mm and approximately 10 mm.

Example 8

The apparatus of any one or more of Examples 1 through 7, wherein the curved portion is configured to position the distal tip at a progressively increasing exit angle relative to a longitudinal axis of the cannula, based on a distance to which the needle is advanced distally relative to the cannula.

Example 9

The apparatus of any one or more of Examples 1 through 8, wherein the curved portion comprises a first curved region and a second curved region, wherein the first curved region is located near a distal portion of the needle, wherein the second curved region is located proximal to the first curved region.

Example 10

The apparatus of Example 9, wherein the first curved region has a first radius of curvature, wherein the second curved region has a second radius of curvature, wherein the second radius of curvature is greater than the first radius of curvature.

Example 11

The apparatus of any one or more of Examples 9 through 10, wherein the first curved region is configured to not impart a curvature to the cannula, wherein the second curved region is configured to impart a curvature to the cannula.

Example 12

The apparatus of any one or more of Examples 1 through 11, wherein the needle further includes a straight proximal portion and a straight distal portion, wherein the curved portion is longitudinally positioned between the straight proximal portion and the straight distal portion.

Example 13

The apparatus of any one or more of Examples 1 through 12, wherein the cannula defines an open distal end.

Example 14

The apparatus of Example 13, wherein the needle is configured to protrude from the open distal end of the cannula when the needle is in the distal position.

Example 15

The apparatus of any one or more of Examples 1 through 14, further comprising a source of liquid therapeutic agent, wherein the needle is operable to deliver the liquid therapeutic agent.

Example 16

The apparatus of Example 15, wherein the body includes: (i) a needle actuator, wherein the actuator is operable to drive the needle longitudinally relative to the cannula, and (ii) a valve member, wherein the valve member is operable to selectively provide fluid communication from the source of liquid therapeutic agent to the needle.

Example 17

An apparatus, comprising: (a) a body; (b) a cannula extending distally from the body, wherein the cannula is flexible, wherein the cannula includes: (i) a closed distal end, and (ii) a lateral opening located proximal to the closed distal end; and (c) a needle slidably disposed in the cannula, wherein the needle includes: (i) a sharp distal tip, wherein the needle is configured to translate relative to the cannula between a proximal position and a distal position, wherein the distal tip is configured to be positioned inside the cannula when the needle is in the proximal position, wherein the distal tip is configured extend past the lateral opening when the needle is in the distal position, and (ii) a curved portion, wherein the curved portion is configured to provide an oblique exit angle to a portion of the needle extending past the lateral opening when the needle is in the distal position.

Example 18

The apparatus of Example 17, wherein the curved portion is resiliently biased to assume a curved configuration, wherein the curved portion is further configured to deform to a substantially straight configuration within the cannula when the needle is in the proximal position.

Example 19

A method of administering a therapeutic agent to an eye of a patient, wherein the eye includes a sclera, a choroid, and a retina, the method comprising: (a) inserting a flexible cannula between the sclera and the choroid; (b) advancing a needle relative to the cannula, thereby penetrating the choroid with a distal tip of the needle, wherein the needle includes a preformed curve, wherein the curve guides the needle toward a targeted region of the choroid; and (c) administering the therapeutic agent to a region between the choroid and the retina via the needle.

Example 20

The method of Example 19, wherein the act of advancing the needle includes: (i) advancing the needle to a first longitudinal position relative to the cannula, wherein the needle defines a first exit angle relative to the cannula at the first longitudinal position, and (ii) advancing the needle further distally to a second longitudinal position relative to the cannula, wherein the needle defines a second exit angle relative to the cannula at the second longitudinal position, wherein the second exit angle is greater than the first exit angle.

VI. MISCELLANEOUS

It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of administering a therapeutic agent to an eye of a patient, wherein the eye includes a sclera, a choroid, and a retina, the method comprising:
   (a) inserting a flexible cannula between the sclera and the choroid;
   (b) advancing a needle relative to the cannula, thereby penetrating the choroid with a distal tip of the needle, wherein the needle includes a preformed curve, wherein the curve guides the needle toward a targeted region of the choroid; and
   (c) administering the therapeutic agent to a region between the choroid and the retina via the needle.

2. The method of claim 1, wherein the act of advancing the needle includes:
   (i) advancing the needle to a first longitudinal position relative to the cannula, wherein the needle defines a first exit angle relative to the cannula at the first longitudinal position, and
   (ii) advancing the needle further distally to a second longitudinal position relative to the cannula, wherein the needle defines a second exit angle relative to the cannula at the second longitudinal position, wherein the second exit angle is greater than the first exit angle.

3. The method of claim 1, the flexible cannula including a closed distal end and a lateral opening located proximal to the closed distal end, the act of advancing the needle including advancing the needle out through the lateral opening.

4. The method of claim 3, the flexible cannula having a generally rectangular cross-sectional profile including a flat side, the lateral opening being formed in the flat side.

5. The method of claim 1, the cannula including a distal opening, the act of advancing the needle including advancing the needle out through the distal opening.

6. The method of claim 1, the flexible cannula including an internal ramp feature, the act of advancing the needle including advancing the needle along the internal ramp feature.

7. The method of claim 1, the act of advancing the needle resulting in a portion of the needle being exposed relative to the cannula, at least part of the exposed portion of the needle being bent along a radius of curvature based at least in part on a resilient bias of the needle.

8. The method of claim 7, the radius of curvature being between approximately 4 mm and approximately 15 mm.

9. The method of claim 7, the radius of curvature being between approximately 7 mm and approximately 12 mm.

10. The method of claim 7, the radius of curvature being between approximately 9 mm and approximately 10 mm.

11. The method of claim 7, the exposed portion of the needle further including a straight portion and a bent portion, the bent portion being bent along the radius of curvature.

12. The method of claim 11, the straight portion being distal to the bent portion.

13. The method of claim 1, the act of advancing the needle resulting in a portion of the needle being exposed relative to the cannula, the exposed portion of the needle including a first bent portion and a second bent portion, the first bent portion being resiliently biased to bend along a first radius of curvature, the second bent portion being resiliently biased to bend along a second radius of curvature.

14. The method of claim 1, further comprising administering a leading bleb fluid to the region between the choroid and the retina via the needle.

15. The method of claim 14, the leading bleb fluid being administered before the therapeutic agent.

16. The method of claim 14, the leading bleb fluid and the therapeutic agent being administered without removing the needle from the choroid between the acts of administering the leading bleb fluid and administering the therapeutic agent.

17. The method of claim 1, the act of advancing the needle resulting in the distal tip of the needle reaching a subretinal space between the choroid and the retina, without the distal tip of the needle penetrating the retina.

18. A method of delivering fluid to an eye of a patient, wherein the eye includes a sclera, a choroid, and a retina, the method comprising:
   (a) inserting a flexible cannula between the sclera and the choroid;
   (b) advancing a needle relative to the cannula while the cannula remains positioned between the sclera and the choroid, wherein a distal tip of the advanced needle penetrates the choroid, wherein the needle includes a preformed curve, wherein the curve guides the distal tip toward a subretinal space between the choroid and the retina; and
   (c) administering the fluid to the subretinal space via the advanced needle.

19. The method of claim 18, the act of administering the fluid comprising:
   (i) administering a first kind of fluid to the subretinal space, and
   (ii) administering a second kind of fluid to the subretinal space after administering the first kind of fluid to the subretinal space, wherein the needle remains stationary within the eye during and between the acts of administering the first kind of fluid and administering the second kind of fluid.

20. A method of delivering fluid to an eye of a patient, wherein the eye includes a sclera, a choroid, and a retina, the method comprising:
   (a) inserting a flexible cannula between the sclera and the choroid;
   (b) advancing a needle relative to the cannula while the cannula remains positioned between the sclera and the choroid, thereby exposing a portion of the needle relative to the cannula, wherein the exposed portion of the needle includes a distal tip, a straight portion, and a curved portion resiliently biased to bend along a curve, wherein the distal tip of the advanced needle penetrates the choroid, wherein the curve guides the distal tip toward a subretinal space between the choroid and the retina; and (c) administering the fluid to the subretinal space via the advanced needle.

\* \* \* \* \*